(12) United States Patent
Liu et al.

(10) Patent No.: US 9,102,931 B1
(45) Date of Patent: Aug. 11, 2015

(54) YEAST STRAINS AND METHOD FOR LIGNOCELLULOSE TO ETHANOL PRODUCTION

(75) Inventors: Zonglin L. Liu, Peoria, IL (US); Jaewoong Moon, Andover, MA (US); Patricia J. Slininger, Metamora, IL (US); Menggen Ma, Wenjiang (CN)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 474 days.

(21) Appl. No.: 13/563,868

(22) Filed: Aug. 1, 2012

(51) Int. Cl.
| | |
|---|---|
| *C12N 1/14* | (2006.01) |
| *C12N 9/90* | (2006.01) |
| *C12N 15/00* | (2006.01) |
| *C12N 1/20* | (2006.01) |
| *C12P 7/06* | (2006.01) |
| *C07H 21/04* | (2006.01) |
| *C12N 15/79* | (2006.01) |

(52) U.S. Cl.
CPC . *C12N 9/90* (2013.01); *C12N 15/79* (2013.01)

(58) Field of Classification Search
CPC .......... C12N 9/90; C12N 15/79; C07K 14/00; C12P 7/06
See application file for complete search history.

(56) References Cited

PUBLICATIONS

Madhavan et al. Xylose isomerase from polycentric fungus *Orpinomyces*: gene sequencing, cloning, and expression in *Saccharomyces cerevisiae* for bioconversion of xylose to ethanol. Appl Microbiol Biotechnol. Apr. 2009;82(6):1067-78. doi: 10.1007/s00253-008-1794-6. Epub Dec. 3, 2008.*

* cited by examiner

*Primary Examiner* — Yong Pak
(74) *Attorney, Agent, or Firm* — John Fado; Albert Y. Tsui; Lesley Shaw

(57) ABSTRACT

Disclosed is a method to incorporate xylose transport related genes into a yeast strain for lignocelluloses to ethanol production. More specifically, the invention relates to novel *Saccharomyces cerevisiae* strains NRRL Y-50463 and yeast strains having novel xylose transporter genes, the genes deposited as GenBank JF343555, GenBank JF343556, GenBank JF343557, GenBank JF343558, and GenBank JF343559. The yeast strains having said genes are deposited as Y-50465, Y-50466, Y-50746, Y-50747, Y-50748, and Y-50749.

5 Claims, 15 Drawing Sheets

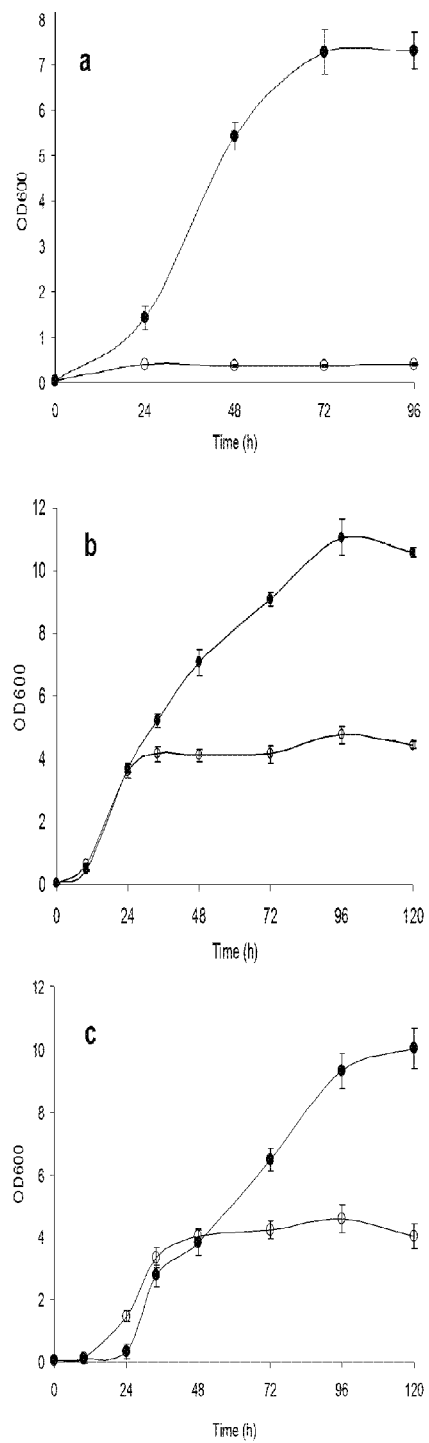
FIGS. 2A-C

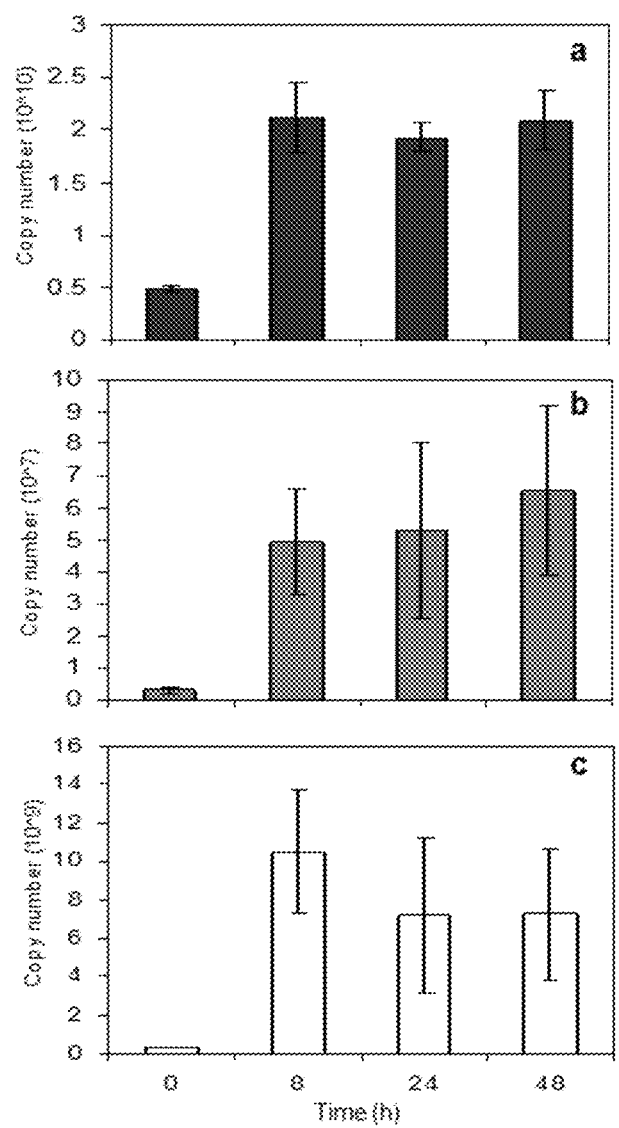
FIGS. 3A-C

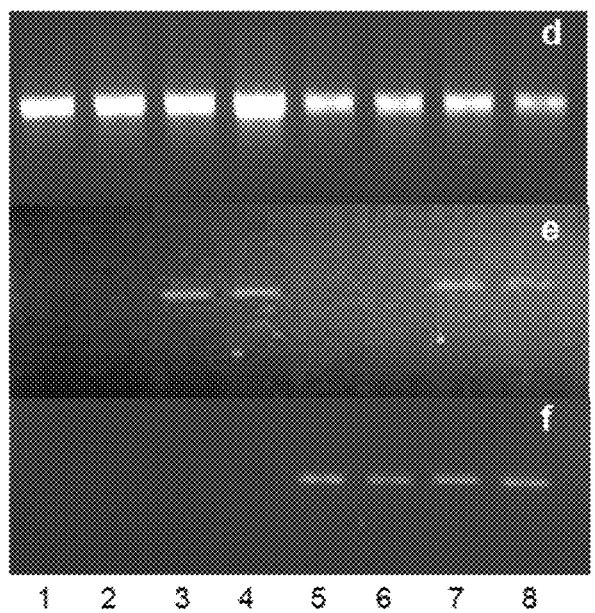
FIGS. 3D-F

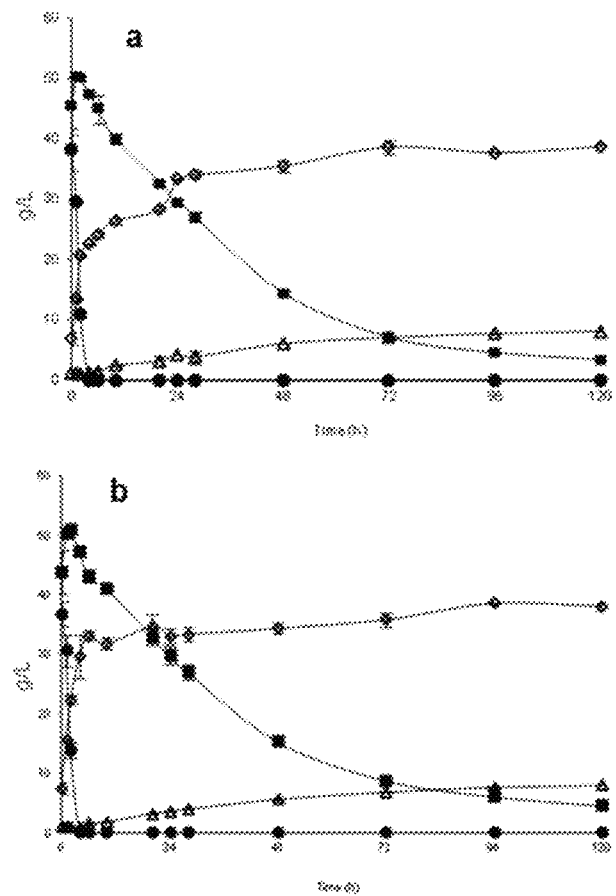
FIGS. 5 A-B

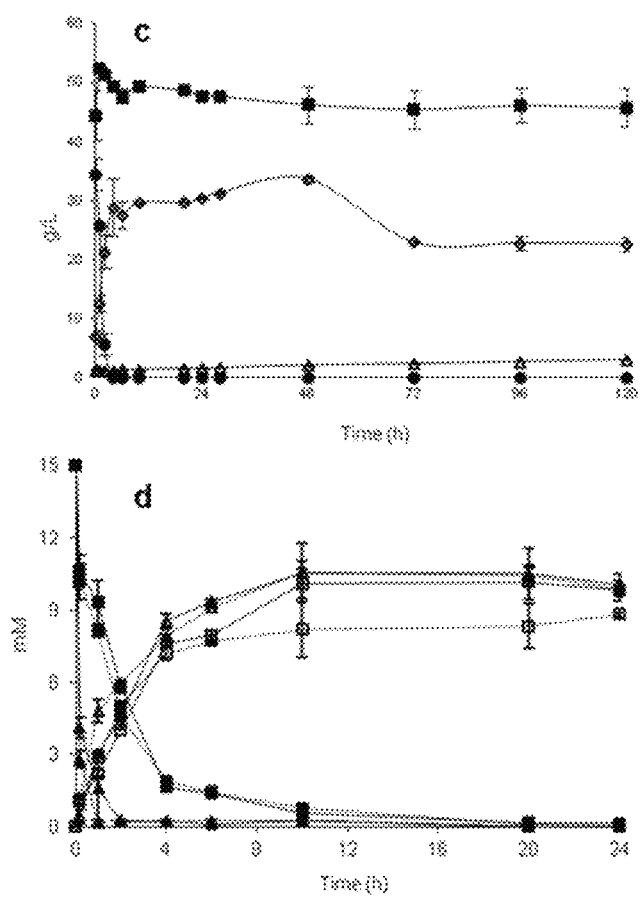
FIGS. 5 C-D

SEQUENCE LISTING

<160> NUMBER OF SEQ ID NOS: 69

<210> SEQ ID NO 1
<211> LENGTH: 30
<212> TYPE: DNA
<213> ORGANISM: Artificial Sequence
<220> FEATURE:
<223> OTHER INFORMATION: Primer XylA_F

<400> SEQUENCE: 1
gcccgcggat gaaaaattac tttccaaatg                               30

<210> SEQ ID NO 2
<211> LENGTH: 33
<212> TYPE: DNA
<213> ORGANISM: Artificial Sequence
<220> FEATURE:
<223> OTHER INFORMATION: Primer XylA_R

<400> SEQUENCE: 2
gcccgcggtt atctaaataa aatattattt acg                           33

<210> SEQ ID NO 3
<211> LENGTH: 43
<212> TYPE: DNA
<213> ORGANISM: Artificial Sequence
<220> FEATURE:
<223> OTHER INFORMATION: Primer YXI_L

<400> SEQUENCE: 3
gcgcgcatgc atatgaagaa ctacttccca aacgttccag aag          43

<210> SEQ ID NO 4
<211> LENGTH: 48
<212> TYPE: DNA
<213> ORGANISM: Artificial Sequence
<220> FEATURE:
<223> OTHER INFORMATION: Primer YXI_R

<400> SEQUENCE: 4
gcgcgcccgc ggttatctga acaaaatgtt gttaacaatg gtttccaa     48

<210> SEQ ID NO 5
<211> LENGTH: 30
<212> TYPE: DNA
<213> ORGANISM: Artificial Sequence
<220> FEATURE:
<223> OTHER INFORMATION: Primer XUT4_L

<400> SEQUENCE: 5
ttttagacaa tgatttcagc tggaggagcc                         30

<210> SEQ ID NO 6
<211> LENGTH: 42
<212> TYPE: DNA
<213> ORGANISM: Artificial Sequence
<220> FEATURE:
<223> OTHER INFORMATION: Primer XUT4_R

<400> SEQUENCE: 6
gcgcgcaagc ttttattcca tctcattcaa cttgtactta aa           42

<210> SEQ ID NO 7
<211> LENGTH: 36
<212> TYPE: DNA
<213> ORGANISM: Artificial Sequence
<220> FEATURE:
<223> OTHER INFORMATION: Primer XUT6_L

<400> SEQUENCE: 7
gcgcgcacta gtatgtccag tgttgaaaaa agtgct                  36

<210> SEQ ID NO 8
<211> LENGTH: 36
<212> TYPE: DNA
<213> ORGANISM: Artificial Sequence
<220> FEATURE:
<223> OTHER INFORMATION: Primer XUT6_R

<400> SEQUENCE: 8
gcgcgccccg ggttagctga tgttttcgac atgctc                  36

<210> SEQ ID NO 9
<211> LENGTH: 35
<212> TYPE: DNA
<213> ORGANISM: Artificial Sequence
<220> FEATURE:
<223> OTHER INFORMATION: Primer XKS1_L

<400> SEQUENCE: 9
gcaagcttat gaccactacc ccatttgatg ctcca                                    35

<210> SEQ ID NO 10
<211> LENGTH: 40
<212> TYPE: DNA
<213> ORGANISM: Artificial Sequence
<220> FEATURE:
<223> OTHER INFORMATION: Primer XKS1_R

<400> SEQUENCE: 10
gcttaattaa attttagtgt ttcaattcac tttccatctt                               40

<210> SEQ ID NO 11
<211> LENGTH: 37
<212> TYPE: DNA
<213> ORGANISM: Artificial Sequence
<220> FEATURE:
<223> OTHER INFORMATION: Primer XYL2_L

<400> SEQUENCE: 11
gcgaattcat gactgctaac ccttccttgg tgttgaa                                  37

<210> SEQ ID NO 12
<211> LENGTH: 37
<212> TYPE: DNA
<213> ORGANISM: Artificial Sequence
<220> FEATURE:
<223> OTHER INFORMATION: Primer XYL2_R

<400> SEQUENCE: 12
ccgcggccgc ttactcaggg ccgtcaatga gacactt                                  37

<210> SEQ ID NO 13
<211> LENGTH: 32
<212> TYPE: DNA
<213> ORGANISM: Artificial Sequence
<220> FEATURE:
<223> OTHER INFORMATION: Primer ADH1_pL

<400> SEQUENCE: 13
gttgcgtcac tagttgcatt atggacttcc tc                                       32

<210> SEQ ID NO 14
<211> LENGTH: 49
<212> TYPE: DNA
<213> ORGANISM: Artificial Sequence
<220> FEATURE:
<223> OTHER INFORMATION: Primer ADH1_pR

<400> SEQUENCE: 14
cttcaaccgc ggataggcca tcaggataga catatgcatt gagatagtt                     49

<210> SEQ ID NO 15
<211> LENGTH: 24
<212> TYPE: DNA
<213> ORGANISM: Artificial Sequence
<220> FEATURE:
<223> OTHER INFORMATION: Primer CYC1_tL

<400> SEQUENCE: 15
gatggccttt ccgcggttga agaa                                                24

<210> SEQ ID NO 16
<211> LENGTH: 24

```
<212> TYPE: DNA
<213> ORGANISM: Artificial Sequence
<220> FEATURE:
<223> OTHER INFORMATION: Primer CYC1_tR

<400> SEQUENCE: 16
ggaagcgatg ttaacagcga cgat                                            24

<210> SEQ ID NO 17
<211> LENGTH: 38
<212> TYPE: DNA
<213> ORGANISM: Artificial Sequence
<220> FEATURE:
<223> OTHER INFORMATION: Primer PGK_pL

<400> SEQUENCE: 17
gcgcgcggta cccgacggct cacaggtttt gtaacaag                             38

<210> SEQ ID NO 18
<211> LENGTH: 56
<212> TYPE: DNA
<213> ORGANISM: Artificial Sequence
<220> FEATURE:
<223> OTHER INFORMATION: Primer PGK_pR

<400> SEQUENCE: 18
gcgcgcctcg agtgttttat atttgttgta aaaagtagat aattacttcc ttgatg         56

<210> SEQ ID NO 19
<211> LENGTH: 45
<212> TYPE: DNA
<213> ORGANISM: Artificial Sequence
<220> FEATURE:
<223> OTHER INFORMATION: Primer PGK_tL

<400> SEQUENCE: 19
gcgcgcccgc ggattgaatt gaattgaaat cgatagatca atttt                     45

<210> SEQ ID NO 20
<211> LENGTH: 39
<212> TYPE: DNA
<213> ORGANISM: Artificial Sequence
<220> FEATURE:
<223> OTHER INFORMATION: Primer PGK_tR

<400> SEQUENCE: 20
gcgcgcgagc tcttcaagct tacacaacac ggtttattt                            39

<210> SEQ ID NO 21
<211> LENGTH: 33
<212> TYPE: DNA
<213> ORGANISM: Artificial Sequence
<220> FEATURE:
<223> OTHER INFORMATION: Primer PDC1_pL

<400> SEQUENCE: 21
gccagctgaa cacaccccgc gtttatttac cta                                  33

<210> SEQ ID NO 22
<211> LENGTH: 40
<212> TYPE: DNA
<213> ORGANISM: Artificial Sequence
<220> FEATURE:
<223> OTHER INFORMATION: Primer PDC1_pR

<400> SEQUENCE: 22
```
gcaagcttga gctctgattt gactgtgtta ttttgcgtga                          40

<210> SEQ ID NO 23
<211> LENGTH: 41
<212> TYPE: DNA
<213> ORGANISM: Artificial Sequence
<220> FEATURE:
<223> OTHER INFORMATION: Primer PDC1_tL

<400> SEQUENCE: 23
gcaagcttca ttaattaaat tgaaatcatg ttgccagtct t                        41

<210> SEQ ID NO 24
<211> LENGTH: 34
<212> TYPE: DNA
<213> ORGANISM: Artificial Sequence
<220> FEATURE:
<223> OTHER INFORMATION: Primer PDC1_tR

<400> SEQUENCE: 24
gcggtaccaa ccattatttg tatcgaggtg tcta                                34

<210> SEQ ID NO 25
<211> LENGTH: 34
<212> TYPE: DNA
<213> ORGANISM: Artificial Sequence
<220> FEATURE:
<223> OTHER INFORMATION: Primer TDH2_pL

<400> SEQUENCE: 25
gcggtacctg agccgatcta aatacttctg tgtt                                34

<210> SEQ ID NO 26
<211> LENGTH: 33
<212> TYPE: DNA
<213> ORGANISM: Artificial Sequence
<220> FEATURE:
<223> OTHER INFORMATION: Primer TDH2_pR

<400> SEQUENCE: 26
gcgaattctt tgttttgttt gtttgtgtga tga                                 33

<210> SEQ ID NO 27
<211> LENGTH: 42
<212> TYPE: DNA
<213> ORGANISM: Artificial Sequence
<220> FEATURE:
<223> OTHER INFORMATION: Primer TDH2_tL

<400> SEQUENCE: 27
ccgcggccgc actccttaag ttactttaat gatttagttt tt                       42

<210> SEQ ID NO 28
<211> LENGTH: 30
<212> TYPE: DNA
<213> ORGANISM: Artificial Sequence
<220> FEATURE:
<223> OTHER INFORMATION: Primer TDH2_tR

<400> SEQUENCE: 28
gcctcgaggc gaaaagccaa ttagtgtgat                                     30

<210> SEQ ID NO 29
<211> LENGTH: 28
<212> TYPE: DNA
<213> ORGANISM: Artificial Sequence

```
<220> FEATURE:
<223> OTHER INFORMATION: Primer ADH2-1a_F.

<400> SEQUENCE: 29
gcctgcagag gtgccggtgt cgttgtcg                                    28

<210> SEQ ID NO 30
<211> LENGTH: 32
<212> TYPE: DNA
<213> ORGANISM: Artificial Sequence
<220> FEATURE:
<223> OTHER INFORMATION: Primer ADH2-1a_R

<400> SEQUENCE: 30
gcgtcgacca gcgtcagcgg tagcgtattc tt                               32

<210> SEQ ID NO 31
<211> LENGTH: 30
<212> TYPE: DNA
<213> ORGANISM: Artificial Sequence
<220> FEATURE:
<223> OTHER INFORMATION: Primer ADH2-2_F

<400> SEQUENCE: 31
gcgttaacgc gcggtgccca cggtatcatc                                  30

<210> SEQ ID NO 32
<211> LENGTH: 38
<212> TYPE: DNA
<213> ORGANISM: Artificial Sequence
<220> FEATURE:
<223> OTHER INFORMATION: Primer ADH2-2a_R

<400> SEQUENCE: 32
ggaagcggaa gagcgttccc cacgtaagag ccgacaat                         38

<210> SEQ ID NO 33
<211> LENGTH: 20
<212> TYPE: DNA
<213> ORGANISM: Artificial Sequence
<220> FEATURE:
<223> OTHER INFORMATION: Primer qYXIp_L

<400> SEQUENCE: 33
aacattaccg acccaatgga                                             20

<210> SEQ ID NO 34
<211> LENGTH: 20
<212> TYPE: DNA
<213> ORGANISM: Artificial Sequence
<220> FEATURE:
<223> OTHER INFORMATION: Primer qYXIp_R

<400> SEQUENCE: 34
caccttctgg agcaatgtca                                             20

<210> SEQ ID NO 35
<211> LENGTH: 20
<212> TYPE: DNA
<213> ORGANISM: Artificial Sequence
<220> FEATURE:
<223> OTHER INFORMATION: Primer qXKS1_L

<400> SEQUENCE: 35
cgaaggtgac attgcctctt                                             20
```

```
<210> SEQ ID NO 36
<211> LENGTH: 20
<212> TYPE: DNA
<213> ORGANISM: Artificial Sequence
<220> FEATURE:
<223> OTHER INFORMATION: Primer qXKS1_R

<400> SEQUENCE: 36
agccaaaggc aacgagataa                                               20

<210> SEQ ID NO 37
<211> LENGTH: 20
<212> TYPE: DNA
<213> ORGANISM: Artificial Sequence
<220> FEATURE:
<223> OTHER INFORMATION: Primer qXYL2_L

<400> SEQUENCE: 37
gatcaaggct ttcggtggta                                               20

<210> SEQ ID NO 38
<211> LENGTH: 20
<212> TYPE: DNA
<213> ORGANISM: Artificial Sequence
<220> FEATURE:
<223> OTHER INFORMATION: Primer qXYL2_R

<400> SEQUENCE: 38
accgacttga acgaaacgac                                               20

<210> SEQ ID NO 39
<211> LENGTH: 20
<212> TYPE: DNA
<213> ORGANISM: Artificial Sequence
<220> FEATURE:
<223> OTHER INFORMATION: Primer qXUT4_L

<400> SEQUENCE: 39
taggtgacat cgttggcaga                                               20

<210> SEQ ID NO 40
<211> LENGTH: 20
<212> TYPE: DNA
<213> ORGANISM: Artificial Sequence
<220> FEATURE:
<223> OTHER INFORMATION: Primer qXUT4_R

<400> SEQUENCE: 40
gcaataccgg caatcaatct                                               20

<210> SEQ ID NO 41
<211> LENGTH: 20
<212> TYPE: DNA
<213> ORGANISM: Artificial Sequence
<220> FEATURE:
<223> OTHER INFORMATION: Primer qXUT6_L

<400> SEQUENCE: 41
gctcttgtca tggctggttt                                               20

<210> SEQ ID NO 42
<211> LENGTH: 20
<212> TYPE: DNA
<213> ORGANISM: Artificial Sequence
<220> FEATURE:
<223> OTHER INFORMATION: Primer qXUT6_R
```

```
<400> SEQUENCE: 42
agacgccgaa gaatgagttg                                              20

<210> SEQ ID NO 43
<211> LENGTH: 42
<212> TYPE: DNA
<213> ORGANISM: Artificial Sequence
<220> FEATURE:
<223> OTHER INFORMATION: Primer XUT4_P_L.

<400> SEQUENCE: 43
gcgcgcctgc agatgtcttc gttattgact aacgaatact tc                     42

<210> SEQ ID NO 44
<211> LENGTH: 42
<212> TYPE: DNA
<213> ORGANISM: Artificial Sequence
<220> FEATURE:
<223> OTHER INFORMATION: Primer XUT4_H_R

<400> SEQUENCE: 44
gcgcgcaagc ttttattcca tctcattcaa cttgtactta aa                     42

<210> SEQ ID NO 45
<211> LENGTH: 36
<212> TYPE: DNA
<213> ORGANISM: Artificial Sequence
<220> FEATURE:
<223> OTHER INFORMATION: Primer XUT6_P_L

<400> SEQUENCE: 45
gcgcgcctgc agatgtccag tgttgaaaaa agtgct                            36

<210> SEQ ID NO 46
<211> LENGTH: 36
<212> TYPE: DNA
<213> ORGANISM: Artificial Sequence
<220> FEATURE:
<223> OTHER INFORMATION: Primer XUT6_Sm_R

<400> SEQUENCE: 46
gcgcgccccg ggttagctga tgttttcgac atgctc                            36

<210> SEQ ID NO 47
<211> LENGTH: 42
<212> TYPE: DNA
<213> ORGANISM: Artificial Sequence
<220> FEATURE:
<223> OTHER INFORMATION: Primer XUT4_X_L

<400> SEQUENCE: 47
gcgcgcctcg agatgtcttc gttattgact aacgaatact tc                     42

<210> SEQ ID NO 48
<211> LENGTH: 42
<212> TYPE: DNA
<213> ORGANISM: Artificial Sequence
<220> FEATURE:
<223> OTHER INFORMATION: Primer XUT4_S_R

<400> SEQUENCE: 48
gcgcgcccgc ggttattcca tctcattcaa cttgtactta aa                     42

<210> SEQ ID NO 49
```

<211> LENGTH: 32
<212> TYPE: DNA
<213> ORGANISM: Artificial Sequence
<220> FEATURE:
<223> OTHER INFORMATION: Primer XUT5_S_L

<400> SEQUENCE: 49
gcgcgcgtcg acatgacgga aagaagcatt gg                                  32

<210> SEQ ID NO 50
<211> LENGTH: 42
<212> TYPE: DNA
<213> ORGANISM: Artificial Sequence
<220> FEATURE:
<223> OTHER INFORMATION: Primer XUT5_EV_R

<400> SEQUENCE: 50
gcgcgcgata tcttacttct ttgtattaac aacaaaacct tg                       42

<210> SEQ ID NO 51
<211> LENGTH: 36
<212> TYPE: DNA
<213> ORGANISM: Artificial Sequence
<220> FEATURE:
<223> OTHER INFORMATION: Primer XUT6_Sm_L

<400> SEQUENCE: 51
gcgcgccccg ggatgtccag tgttgaaaaa agtgct                              36

<210> SEQ ID NO 52
<211> LENGTH: 36
<212> TYPE: DNA
<213> ORGANISM: Artificial Sequence
<220> FEATURE:
<223> OTHER INFORMATION: Primer XUT6_S_R

<400> SEQUENCE: 52
gcgcgcacta gtttagctga tgttttcgac atgctc                              36

<210> SEQ ID NO 53
<211> LENGTH: 39
<212> TYPE: DNA
<213> ORGANISM: Artificial Sequence
<220> FEATURE:
<223> OTHER INFORMATION: Primer XUT7_S_L

<400> SEQUENCE: 53
gcgcgcgtcg acatgacttt tgcagttaac ttgtatgtg                           39

<210> SEQ ID NO 54
<211> LENGTH: 36
<212> TYPE: DNA
<213> ORGANISM: Artificial Sequence
<220> FEATURE:
<223> OTHER INFORMATION: Primer XUT7_B_R

<400> SEQUENCE: 54
gcgcgcggat ccttagtcca aatcgtccaa atcgtc                              36

<210> SEQ ID NO 55
<211> LENGTH: 36
<212> TYPE: DNA
<213> ORGANISM: Artificial Sequence
<220> FEATURE:
<223> OTHER INFORMATION: Primer RGT2_S_L

<400> SEQUENCE: 55
gcgcgcgtcg acatgggttt agaagacagt gctctc                                    36

<210> SEQ ID NO 56
<211> LENGTH: 39
<212> TYPE: DNA
<213> ORGANISM: Artificial Sequence
<220> FEATURE:
<223> OTHER INFORMATION: Primer RGT2_EV_R

<400> SEQUENCE: 56
gcgcgcgata tcctatacag aagcttcttc aacttcaga                                 39

<210> SEQ ID NO 57
<211> LENGTH: 36
<212> TYPE: DNA
<213> ORGANISM: Artificial Sequence
<220> FEATURE:
<223> OTHER INFORMATION: Primer SUT4_S_L

<400> SEQUENCE: 57
gcgcgcgtcg acatgtcctc acaagattta ccctcg                                    36

<210> SEQ ID NO 58
<211> LENGTH: 39
<212> TYPE: DNA
<213> ORGANISM: Artificial Sequence
<220> FEATURE:
<223> OTHER INFORMATION: Primer SUT4_B_R

<400> SEQUENCE: 58
gcgcgcggat ccctaaactt gctcttgctc ttttgtttc                                 39

<210> SEQ ID NO 59
<211> LENGTH: 38
<212> TYPE: DNA
<213> ORGANISM: Artificial Sequence
<220> FEATURE:
<223> OTHER INFORMATION: Primer PGK_PL

<400> SEQUENCE: 59
gcgcgcggta cccgacggct cacaggtttt gtaacaag                                  38

<210> SEQ ID NO 60
<211> LENGTH: 55
<212> TYPE: DNA
<213> ORGANISM: Artificial Sequence
<220> FEATURE:
<223> OTHER INFORMATION: Primer PGK_PR

<400> SEQUENCE: 60
gcgcgcctcg agtgttttat atttgttgta aaaagtagat aattattcct tgatg              55

<210> SEQ ID NO 61
<211> LENGTH: 45
<212> TYPE: DNA
<213> ORGANISM: Artificial Sequence
<220> FEATURE:
<223> OTHER INFORMATION: Primer PGK_TL

<400> SEQUENCE: 61
gcgcgcccgc ggattgaatt gaattgaaat cgatagatca atttt                          45

<210> SEQ ID NO 62
<211> LENGTH: 39
<212> TYPE: DNA

```
<213> ORGANISM: Artificial Sequence
<220> FEATURE:
<223> OTHER INFORMATION: Primer PGK_TR

<400> SEQUENCE: 62
gcgcgcgagc tcttcaagct tacacaacac ggtttattt                              39

<210> SEQ ID NO 63
<211> LENGTH: 1317
<212> TYPE: DNA
<213> ORGANISM: Artificial Sequence
<220> FEATURE:
<223> OTHER INFORMATION: cDNA of the gene YXI

<400> SEQUENCE: 63
atgaagaact acttcccaaa cgttccagaa gttaagtacg aaggtccaaa ctctaccaac       60
ccattcgctt tcaagtacta cgacgctaac aaggttgttg ctggtaagac catgaaggaa      120
cactgtagat tcgctttgtc ttggtggcac accttgtgtg ctggtggtgc tgacccattc      180
ggtgttacca ccatggacag aacctacggt aacattaccg acccaatgga attggctaag      240
gctaaggttg acgctggttt cgaattgatg accaagttgg gtattgaatt cttctgtttc      300
cacgacgctg acattgctcc agaaggtgac accttcgaag aatctaagaa gaacttgttc      360
gaaattgttg actacattaa ggaaaagatg gaccaaaccg gtattaagtt gttgtggggt      420
accgctaaca cttctctca cccaagattc atgcacggtg cttctacctc ttgtaacgct       480
gacgttttcg cttacgctgc tgctaagatt aagaacgctt tggacgctac cattaagttg      540
ggtggtaagg gttacgtttt ctggggtggt agagaaggtt acgaaacctt gttgaacacc      600
gacttgggtt tggaattgga caacatggct agattgatga gatggctgt tgaatacggt      660 agagctaacg gttcgacgg tgacttctac attgaaccaa agccaaagga accaaccaag      720
caccaatacg acttcgacac cgctaccgtt ttggctttct gagaaagta cggtttggaa       780 aaggacttca gatgaacat tgaagctaac cacgctacct ggctggtca caccttcgaa       840 cacgaattgg ctatggctag agttaacggt gctttcggtt ctgttgacgc taaccaaggt      900
gacccaaact tgggttggga caccgaccaa ttcccaaccg acgttcactc tgctaccttg      960
gctatgttgg aagttttgaa ggctggtggt ttcaccaacg gtggtttgaa cttcgacgct     1020
aaggttagaa gaggttcttt cgaattcgac gacattgctt acggttacat tgctggtatg     1080
gacaccttcg ctttgggttt tgattaaggct gctgaaatta ttgacgacgg tagaattgct     1140
aagttcgttg acgacagata cgcttcttac aagaccggta ttggtaaggc tattgttgac     1200
ggtaccacct ctttggaaga attggaacaa tacgttttga cccactctga accagttatg     1260
caatctggta gacaagaagt tttggaaacc attgttaaca acattttgtt cagataa        1317

<210> SEQ ID NO 64
<211> LENGTH: 1690
<212> TYPE: DNA
<213> ORGANISM: Artificial Sequence
<220> FEATURE:
<223> OTHER INFORMATION: cDNA of the xylose transporter gene RGT2

<400> SEQUENCE: 64
attatctact ttttacacaa atataaaaca ctcgaggtcg acatgggttt agaagacagt       60
gctctcttgc aaaagtacat caacttcggt gaaagaaggg ctggttccac caccatgggt      120
atctgtgttg gtttgttcgc agccttcggt ggtatccttt tcggttatga cactggtacc      180
atctccggta tcatggccat ggactacgtc actgccagat tcccatccaa ccaccaatct      240
```

```
ttcagttctt ctgaatcttc ccttattgtt tccattttgt ctgttggtac cttctttggt    300
tctctttctg catctttcat ctccgacaga ttgggtcgta gattgacttt aatgatctcc    360
accttgatca tcttcaatgt cggtattatc ttgcaaactg cctctactag cattccactt    420
ttgtgtgttg gtagagtttt tgctggtctt ggtgttggtc tcatttccgc tgttattcca    480
ttgtaccaag ctgaaacagt tccaaagtgg atcagaggtg ctgttgtctc ctgttaccaa    540
tgggccatta cccttggttt gttgttggct gctgttgtta accaaggtac ccacaacaga    600
aatgactctg gttcctacag aatcccaatt gctatccaat tcttgtgggc tttgattttg    660
ggaggtggta tgtgtttgtt gccagaaacc ccaagattct gggtttctaa aggtgacaac    720
gacagagcca aggactcctt gagaagattg agaaagttgc ccctcgacca tcccgacttg    780
attgaagaat acgaagaaat caaggctaac tacgaatacg aagctcaata cggttcaggt    840
tcttggagtc aagttttgc taacaagaac caccaaagaa agagattggc catgggtgtt    900
ggtatccaag ccttgcaaca attgaccggt attaactta tcttctacta tggtactaac    960
ttcttcaagg gttctggtat caaaaacgaa ttccttatcc aaatggccac taacattgtc   1020
aacttcggtt ctactgtccc aggtattctt tggttgaaaa ttattggtag aagaaagttg   1080
ttgttgggtg gttctgcagt tatgtccatt tctcaattga ttgttgctat tgtcggtgtt   1140
gccgctggtg aaggttcaac ttctgccaac aagtgtttgg ttgccttcgt ttgtatcttc   1200
attgctgctt tcgcagccac ttggggtcct ctttgttggg ctgtcattgc cgaatgttac   1260
ccacttacag ttagacaaaa gtccatctcc ttgtgtacag cttccaactg gttgtggaac   1320
tggggtattg cctacgctac tccttacatg gtcaactccg gtccaggtaa cgccaacttg   1380
ggttccaagg ttttcttcat ctggggtggt tgtaatatca ttggtggtct tttcgtgtgg   1440
taccttgtct acgaaactaa gggcttgacc ttagaacaaa tcgatgaaat gtacgaaaag   1500
gttccaaagg cttggcaatc taccagattc attccatccg aacatgcatt cactcaacca   1560
tccgcagctg cctctgtctc ttctggtaag gctgaaggtg tttctgaagt tgaagaagct   1620
tctgtatagg atatcgaatt cctgcagccc gggggatcca ctagttctag agcggccgcc   1680
accgcggatg                                                           1690
```

<210> SEQ ID NO 65
<211> LENGTH: 1346
<212> TYPE: DNA
<213> ORGANISM: Artificial Sequence
<220> FEATURE:
<223> OTHER INFORMATION: cDNA of the xylose transporter gene XUT7

<400> SEQUENCE: 65

```
tatctacttt ttcaacaaat ataaaacact cgaggtcgac atgactttg cagttaactt     60 gtatgtgttt gcagttggta gagtgctttc tggggtgggt gtaggagttc tatcgactat    120
ggtgccgtcc tatcaatgcg aaattagtcc cagcgaagaa agaggcaagt tggtgtgtgg    180
agagttcacg ggaaatatca ctggttatgc tctcagtgta tgggccgatt acttctgcta    240
ctttattcaa gatataggtg atgcaaggga gaagcctcat agcttctttg cccacttgtc    300
ctggcgattg cctctattca tccaggtggt gatagcggct gttctctttg ttgggggatt    360
ttttattgtc gagtcaccct cgttggttatt agatgtagac caggaccaac aaggattcca    420
tgtattagcg ttgctctatg attcacatct agatgataac aaaccacgtg aagagttctt    480
tatgatcaag aactccatct tgttagaaag agaaactaca cctaagagcg aacgaacttg    540
```

```
gaaacatatg ttcaagaact acatgacccg agtgcttata gcttgttcag cacttggctt      600
tgcacagttc aacggcataa atatcatttc gtactatgcc cccatggtat ttgaagaagc      660
aggcttcaac aactccaagg ctttacttat gacaggcatc aactctatag tatattggtt      720
cagtacgatt cctccgtggt ttctcgtgga tcattgggt agaaagccaa ttttgatatc       780
cgggggttta tctatgggaa tatgtattgg tttgattgcg gtggtaattc tactagacaa      840
gtcgttcaca ccgtctatgg ttgcggtgtt ggtgataatc tacaatgcat cttttggcta      900
cagttggggt cctatcggat tcttgatccc gccggaggtg atgccattgg cagttagatc      960
gaaaggtgtt tctatttcta cggctacaaa ctggtttgcc aattttgttg tgggtcagat     1020
gacgccaatt ctacagcaga gattgggctg gggaacttat ctattcccgg ctggtagttg     1080
tatcatctcg gtgatagtgg tgattttctt ctatccagag acaaagggtg tagagctaga     1140
ggatatggac tctgtgttcg agagctttta caactacaag tctccgttca agatttcacg     1200
aaagagacac cagaatgatg ccaggcgta ccaaagggta gagaacgata tccgccacaa      1260
cgatgtagaa atggacgatt tggacgattt ggactaagga tccactagtt ctagagcggc     1320
cgccaccgcg gatgaattga atgaaa                                          1346

<210> SEQ ID NO 66
<211> LENGTH: 1595
<212> TYPE: DNA
<213> ORGANISM: Artificial Sequence
<220> FEATURE:
<223> OTHER INFORMATION: cDNA of the xylose transporter gene XUT5

<400> SEQUENCE: 66 acttttcac aaatataaaa cactcgaggt cgacatgacg gaaagaagca ttggaccttt       60
aatccccaga aataagcact tattctatgg atccgtatta tagatgagta ttgttcaccc     120
aactatcatg ggatacgatt ccatgatggt tggtagtatt cttaatctag atgcatatgt     180
aaattatttc cacttaacgg ctgctaccac tggactcaat actgctgcag tatggccttgg   240 gcaagtaatt gccacattga cagttattct gtatttcaat gacaaatttg gtagaagaag    300
ctcagtttgt ataagtattg caatcagttt ggttggggtt gcattgcaat cagcagccca     360
gaacattgag atgtttatta tcggaagaat agttattggt tttggaatat ctattggttt     420
tgtctcatct accatttttgg taagtgaact agccctcca gacaaaagag gatttattct      480
tggattgagt tttacaagct ttctagtagg aagtttaatt gcagcaggtg tcacatatgg     540
aacaagaaat gctcctggag actggtgttg gagaatccca tcaattattc aaggggctcc     600
agatattgtt gctattatta acatactctt tatttcagaa tcaccaaggt ggttgattgc     660
aaaggaaaga ttcagcgaag ctcgtgaaat tatttctatc attagtgatg ttcctattga     720
agatgcacat gaagaatgtg aaaagataca tgcccatatt caaactgaga agactgcttt     780
ccctggcaat aagtggaaac aaatggtgag ctccaagagc aatacaagaa gagttattat     840
cttgttcaca caggccatag ttactgaaat ggccggttct tcagttggat cgtactattt     900
ttcaattata ttaactcaag ctggggtcaa agattcgaat gatagactaa gagtaaatat     960
tgtgatgagt tcgtggtcat tggtaattgc tctttccgga tgtctaatgt ttgacagaat    1020
tggaagaaag atgcaatcgc tcatttcgtt atcaggtatg atcatatgct ttatagtttt    1080
aggtgttttg gttaaagaat atggcgatgg tcatagcaag agcggaagtt acgcagctgt    1140
cgccatgatg tttttattca caggatttta ctcattcact ttcactccat tgaactcttt    1200
gtaccctcca gaattgttcc cctacgtgtt gagaagtaca ggagttacac tctttaatat    1260
```

```
tttcaacggc tgctggggac ttttcgcaag tttcatttta cccattgcaa tgaatggaat    1320
tggctggaaa ttttacatca ttaatgcttg ctatgacgtc atattccttc caataataat    1380
gttctgttgg attgagacaa agggaattaa tttggataca attagtgaag tattgcacgg    1440
aagaggacct gaagatgaag aaagcattga agaaagtcac agcctaatca gacaaggttt    1500
tgttgttaat acaaagaagt aagatatcga attcctgcag cccgggggat ccactagttc    1560
tagagcggcc gccaccgcgg atgaatgaat gaaat                              1595
```

<210> SEQ ID NO 67
<211> LENGTH: 2047
<212> TYPE: DNA
<213> ORGANISM: Artificial Sequence
<220> FEATURE:
<223> OTHER INFORMATION: cDNA of the xylose transporter gene XUT6

<400> SEQUENCE: 67

```
tctggaatgg cgggaaaggg tttagtacca catgctatga tgcccactgt gatctccaga      60
gcaaagttcg ttcgatcgta ctgttactct ctctctttca aacagaattg tccgaatcgt     120
gtgacaacaa cagcctgttc tcacacactc ttttcttcta accaaggggg tggtttagtt     180
tagtagaacc tcgtgaaact tacatttaca tatatataaa cttgcataaa ttggtcaatg     240
caagaaatac atatttggtc ttttctaatt cttagttttt caagttctta gatgctttct     300
ttttctcttt tttacagatc atcaaggaag taattatcta cttttttacac aaatataaaa     360 cactcgagat gtccagtgtt gaaaaaagtg ctgaaactgc ttcctatacg tcgcaggtca     420
gcgcaagcgg ctctgcaaag accaacagct accttggcct cagaggcaac aaacttaatt     480
ttgctgtctc ttgttttgct ggtgttggtt tcttactttt gggttacgat caaggtgtca     540
tgggttcatt gttgaccttg ccatccttcg aaaaacacttt cccggccatg aaggctagca     600
acaacgctac cttacaaggc gccgttattg cactttatga atcggttgt atgtcttctt      660 ctttagcaac catttacctt ggtgacagat tgggtagatt gaagatcatg tttattggct     720
gtgtaattgt ctgtattggt gctgctttgc aagcttctgc tttcactatt gctcacttga     780
ctgttgctag aattatcact ggtttaggta caggtttcat cacttctact gttccagttt     840
accaatcgga gtgctctcca gccaagaaaa gaggacagtt gatcatgatg gaaggttctc     900
ttatcgccct tggcattgcc atctcatact ggattgactt tggattttac ttttttgagaa     960 acgatggttt gcactcctcg gcttcttgga gagcacctat cgcgcttcaa tgtgtcttcg    1020
ctgtcttgtt gatttccaca gtcttcttct cccagaatc tccaagatgg ttgctcaaca    1080
aaggtaggac cgaagaagct agagaagttt ttctgctct ttacgacttg ccagccgact    1140
ctgaaaagat ttctattcaa attgaagaaa ttcaagctgc tatagattta gaaagacaag    1200
ccggagaagg tttcgtactt aaggaattgt tcactcaggg cccagccaga aacttgcagc    1260
gtgtggcctt gtcatgttgg tctcaaataa tgcaacaaat cactggtatt aacattatta    1320
cgtactatgc tggtactatt tttgaatcat acattggtat gagtccattt atgtcaagaa    1380
tcttggctgc cttgaacggt actgaatatt tccttgtctc tcttattgct ttctacaccg    1440
tcgaaagatt aggtagaaga ttccttttgt tctggggtgc catcgccatg gctcttgtca    1500
tggctggttt aactgttacc gttaaacttg ccggtgaagg caacacccat gctggtgtcg    1560
gtgctgctgt tctttttgttt gcattcaact cattcttcgg cgtctcctgg ttaggtggat    1620
cctggttgtt accacctgaa ttgttgtctt tgaaattgag agctcctggt gctgctttgt    1680
```

```
cgaccgcttc taactgggct tttaacttca tggttgtcat gatcactcct gtcggtttcc    1740
aaagtattgg ttcctacacc taccttatct ttgctgccat caatttgttg atggctccgg    1800
tcatctactt cttgtatccc gaaaccaagg gtagatcgtt ggaagaaatg gatatcattt    1860
tcaaccaatg tcctgtttgg gagccatgga aggttgtcca aattgccaga gacctcccta    1920
ttatgcactc agaagttctt gaccacgaaa aggatgtcat tattgaaaaa tctagaatag    1980
agcatgtcga aaacatcagc taaactagtt ctagagcggc cgccaccgcg gatgaatgaa    2040
tgaaatc                                                              2047
```

<210> SEQ ID NO 68
<211> LENGTH: 1674
<212> TYPE: DNA
<213> ORGANISM: Artificial Sequence
<220> FEATURE:
<223> OTHER INFORMATION: cDNA of the xylose transporter gene XUT4

<400> SEQUENCE: 68

```
cacaaatata aaacactcga gatgtcttcg ttattgacta cgaatactt caaagactac      60 taccacaacc cgactcctgt tgaagtgggt actatgattg ctatcttaga gatcggcgca    120
cttttttcct ccttcatagc tggaagagta ggtgacatcg ttggcagaag aagaaccatt    180
agatacgggt cttcattttt tgtagtaggc ggtcttgtac aagctacttc ggtcaatatt    240
gtcaatctct cactaggaag attgattgcc ggtattgcca ttggcttttt gacaaccatc    300
atcccatgct accagtctga aatcagcccc ccagacgata gaggtttcta tgcctgtttg    360
gagttcaccg gaaatatcat tggatatgct agtagtattt gggtagacta cgggttttca    420
tttttagaca tgatttcag ctggaggagc ccattgtatg ttcaggttgt tattggctcc    480 atgttatta ttggttcatt ccttattgta gaaaccccta gatggctctt ggatcacaac    540
catgatatcg aaggcatgat tgtcatttct gacttgtatg cagatggtga tgtggaagac    600
gatgatgcta ttgctgagta cagaaacata aaggaaagtg tcttgatagc cagagttgaa    660
ggcggagaga gatcgtacca gtatttgttc accaaatata ccaagagact ttctgtggca    720
tgcttttcgc aaatgtttgc ccagatgaat ggtataaaca tggtatctta ctatgctcct    780
atgatcttcg aatctgctgg ctgggttggt agacaagcta tcttgatgac tggtatcaac    840
tccattatct acatctttag taccattcct ccatggtact agttgattc ttggggcaga    900 aaacctttgc ttttatctgg atctgtgctc atgggtgttc cgctcttaac cattgcttgt    960
tcgttattct taaacaacac atacacaccc gggggttgtgg ttggcagtgt aatcgtattc    1020
aatgctgctt ttggatacag ttggggtcca attccttggc tcatgagcga agtgttccct    1080
aactcagtta gatcaaaagg tgctgccatg tctactgcaa ccaactggct ctttaacttt    1140
attgttggag agatgacacc tattttgttg gatacaatta cctggagaac ttacttgatc    1200
ccggcaactt cgtgtgtatt atcgtttttt gctgttggat ttttatttcc agagaccaag    1260
ggtttagcat tggaggatat gggctccgta ttcgatgata ttcgtcaat attttcatat    1320 cactcaactc cttccactgg gtatggtgcg accgagtcta acagtaatgc caggagagca    1380
agtgtcatct cttcagaaaa ctaccaggat agtttgcatc agacagcggc ttcattggct    1440
aggaatcctt caagcatgag gcctgattac gatggcataa tcacaggagc tgctacccct    1500
tcgccagtac caccattaaa accaataaag tctgatgcgt cagtccattc agtcgatgcc    1560
ataattccaa gcatttccag caatattccg caggaaattg aaccaccaac ctttgatgaa    1620
gtctttaagt acaagttgaa tgagatggaa taaccgcgga tgaatgaatg aaat          1674
```

<210> SEQ ID NO 69
<211> LENGTH: 1741
<212> TYPE: DNA
<213> ORGANISM: Artificial Sequence
<220> FEATURE:
<223> OTHER INFORMATION: cDNA of the xylose transporter gene SUT4

<400> SEQUENCE: 69

```
tatctacttt ttacacaaat ataaaacact cgaggtcgac atgtcctcac aagatttacc      60
ctcgggtgct caaacccaa tcgatggttc ttccatcctc gaagataaag ttgagcaaag     120
ttcgtcaaat agccaacgtg atttagcttc tattccagca acagatatca aagcctatct     180
cttggtttgt ttcttctgca tgttggttgc cttcggtggc ttcgtattcg gtttcgatac     240
cggtactatt tccggtttcc ttaatatgtc tgatttcctt ccagatttg gtcaagatgg     300
ttctgaagga aaatatttgt ccgatatcag ggttggtttg attgtttcca tttttaacat     360
tggttgtgca attggtggta ttttccttc taagatagga gatgtttacg gtagaagaat     420
tggtatcatt tcagctatgg ttgtctatgt cgtcggtata atcatccaga tctcgtccca     480
agacaagtgg tatcaactta caattggacg tggagttaca ggattagctg ttggtactgt     540
ttcggttttg tctccaatgt tcattagtga aagtgctcca aagcatttga gaggtacttt     600
ggtatactgt taccaattat gcatcaccct aggtattttc attggttact gtgtcactta     660
tggaaccaaa gatttaaatg attcaagaca atggagagtt cctttgggtt tatgtttcct     720
ctgggctatt ttcttagttg tcggtatgtt ggctatgcct gaatccccaa gattcttaat     780
tgaaaagaag agaatcgaag aagccaagaa gtcccttgca agatccaaca agttatctcc     840
agaagatcca ggtgtctaca ctgaagttca attgattcag gctggtattg acagagaagc     900
tgctgcaggt tctgcttcat ggatggaatt gatcactggt aagccagcta ttttcagaag     960
agttatcatg ggaattatct tacagtcttt gcaacaatta actggtgtca actatttctt    1020
ctattacgga actacaatct tccaagctgt tggtttgcaa gattccttcc agacttccat    1080
catcttaggt acagtcaact ttcttttctac atttgttggt atttgggcca ttgaaagatt    1140
tggaagaaga caatgtttgt tagtcggttc tgctggtatg ttcgtttgtt tcatcattta    1200
ctctgtcatt ggtacaactc atttgttcat tgatggagta gtagataacg acaacacccg    1260
tcaactgtct ggtaatgcta tgatctttat cacttgtttg ttcatcttct ctttgcctg    1320
tacttgggct ggaggtgttt ttacaatcat ttccgaatca tatccattga aatcagatc    1380
caaggctatg tctattgcca ctgccgctaa ctggatgtgg ggtttcttga tttcattctg    1440
cactccattc attgttaacg ccatcaactt caagttcggc tttgtgttta ctggttgttt    1500
gctcttttcg ttcttctatg tctacttctt tgtcagcgaa acaaaaggtt tgtcgttgga    1560
agaagttgat gagttgtacg ctgagggaat tgcaccatgg aaatccggtg catgggttcc    1620
tccttctgca caacaacaaa tgcaaaactc tacttatggt gccgaaacaa aagagcaaga    1680
gcaagtttag ggatccacta gttctagagc ggccgccacc gcggatgaat gaatgaaatc    1740
g                                                                   1741
```

YEAST STRAINS AND METHOD FOR LIGNOCELLULOSE TO ETHANOL PRODUCTION

FIELD OF THE INVENTION

This invention relates to a method to incorporate xylose transport related genes into a yeast strain for lignocelluloses to ethanol production. Additionally, the invention relates to novel *Saccharomyces cerevisiae* strains NRRL Y-50463 and yeast strains having xylose transporter genes, the genes deposited as GenBank JF343555, GenBank JF343556, GenBank JF343557, GenBank JF343558, and GenBank JF343559. Novel yeast strains having said genes are deposited as Y-50465, Y-50466, Y-50746, Y-50747, Y-50748, and Y-50749.

BACKGROUND OF INVENTION

There exist two major bottlenecks of technical challenges for economical ethanol production using lignocellulosic biomass as feedstocks. First, inhibitory compounds associated with lignocellulo sic biomass pretreatment, especially by dilute acid hydrolysis, inhibit microbial growth and subsequent fermentation. Major inhibitor include 2-furaldehyde (furfural) and 5-(hydroxymethyl)-2-furaldehyde (HMF) are derived from lignocellulosic hydrolysates. Bacteria and yeast are susceptible and in general unable to grow in the presence of multiple inhibitors even at low concentrations. Another significant technical challenge is to enable and enhance yeast capability in utilization of pentose such as xylose and arabinose harbored in biomass.

Genetic engineering efforts have been made to improve xylose utilization by overexpressing genes encoding pentose phosphate pathway (PPP) enzymes to enhance xylose flux into central carbon metabolism. For native *S. cerevisiae*, there is no xylose-specific transporters available and the xylose uptake is via certain hexose transporters such as Hxt4, Hxt5, Hxt7. Recently, several heterologous sugar transporter genes possessing xylose transport functions have been expressed in *S. cerevisiae* such as SUT1, XUT1 or XUT3 from *S. stipitis*, At5g59250 and At5g17010 from *A. thaliana*, An25 from *N. crassa*, DEHA0D02167 and XylHP from *D. hansenii*, and symporters GXS1 and GXF1 genes from *C. intermedia*. Improvement of xylose utilization by such efforts was observed but a satisfactory level has not been reached. As such, there is a need to further develop ethanologenic yeast that are tolerance to major inhibitors such as aldehydes and to establish xylose transportation systems to facilitate xylose uptake for efficient lignocellulose-to-ethanol conversion.

BRIEF SUMMARY OF THE INVENTION

Disclosed herein are yeast strains expressing both glucose and xylose utilization pathways the ferment both glucose and xylose to ethanol, wherein the genes for the xylose pathway comprise a xylose isomerase gene, a xylulokinase gene, a xylitol dehydrogenase, and at least two xylose transporter genes. In one embodiment of the invention, the yeast strain express xylose transporter genes are XUT4 and XUT6. In another embodiment of the invention, the yeast strain ferments xylose to ethanol at a higher rate than the rate of its parent strain. In yet another embodiment of the invention, the yeast strain is a *Saccharomyces cerevisiae* strain. In one particular embodiment of the invention, the yeast strain is deposited as NRRL Y-50463.

Also disclosed herein is a method of producing ethanol from the fermentation of xylose comprising of culturing the yeast strains Y-50463, Y-50465, Y-50466, Y-50746, Y-50747, Y-50748, or Y-50749 of in xylose-containing material under suitable conditions for a period of time sufficient to allow fermentation of at least a portion of the xylose to ethanol. In one embodiment of the invention the yeast strain ferments both xylose and glucose.

Also disclosed herein are yeast strains expressing both glucose and xylose utilization pathways that ferment both glucose and xylose to ethanol, wherein the genes for the xylose pathway comprise a xylose isomerase gene and a xylose transporter gene. In one embodiment of the invention, the yeast strain expresses the xylose transporter gene of identified in SEQ. ID. Nos. 64, 65, 66, 67, 68, or 69. In another embodiment of the invention, a yeast strain having a yeast strain Y-50049 as a parent strain, expresses both glucose and xylose utilization pathways that ferment both glucose and xylose to ethanol, wherein the genes for the xylose pathway comprise a xylose isomerase gene and a xylose transporter gene, wherein the isomerase gene is integrated into said yeast strain chromosome. In another particular embodiment of the invention, the yeast strains are deposited as NRRL Y-50465, Y-50466, Y-50746, Y-50747, Y-50748, or Y-50749.

BRIEF DESCRIPTION OF THE DRAWINGS

FIG. 2 is a graph depicting the growth performance of engineered *S. cerevisiae* strain NRRL Y-50463 (filled circle) and parental strain Y-50049 (open circle). Comparisons of aerobic growth on YP medium containing 50 g l$^{-1}$ D-xylose as sole carbon source (a), and mixed sugars of 50 g l$^{-1}$ D-glucose and 50 g l$^{-1}$ D-xylose in the absence (b) or the presence (c) of 10 mM each of furfural and HMF.

FIGS. 3A-C depict graphs of transcription analysis of heterologous genes. Graphs of quantitative transcription analysis using gene copy numbers over time of heterologous codon-optimized xylose isomerase gene YXI (FIG. 3A), xylulokinase gene XKS1 (FIG. 3B) and xylitol dehydrogenase gene XYL2 (FIG. 3C) are depicted.

FIGS. 3D-F are photos of electrophoresis gels of qRT-PCR products for YXI (d), xylose transport related gene XUT4 (e) and XUT6 (f) individually and in combination of XUT4-XUT6 (e and f). Lanes of the gel photo are labeled as 1 and 2, YXI; 3 and 4, YXI–XUT4; 5 and 6, YXI–XUT6; and 7 and 8, YXI–XUT4–XUT6.

FIGS. 5A-D depict graphs of anaerobic batch co-fermentation of mixed sugars of either *S. cerevisiae* strain NRRL Y-50463 in the absence (a) or the presence (b) of inhibitors compared with its wild type parent strain Y-50049 (c) on a YP medium containing 50 g l$^{-1}$ D-glucose, 50 g l$^{-1}$ D-xylose, 15 mM furfural, and 15 mM HMF. Figure legends are labeled as glucose (filled circle), xylose (filled square), ethanol (open diamond), and xylitol (open triangle). Inhibitor conversions during the fermentation (d) for strain Y-50463 (solid line) and Y-50049 (dotted line) showing rapid reduction of furfural (filled triangle) and HMF (filled square), and corresponding conversion products of furanmethanol (open triangle) and furandimethanol (open square).

FIG. 7A depicts a graph comparing of cell growth of S. cerevisiae Y-50049–YXI (filled circle) and its enriched genotypes with varied xylose transporter genes using xylose as sole carbon source under aerobic conditions over time (hours). The yeast strain are labeled as Y-50049–YXI–XUT4 (filled triangle), Y-50049–YXI–XUT5 (filled diamond), Y-50049–YXI–XUT6 (filled square), Y-50049–YXI–XUT7 (open circle), Y-50049–YXIRGT2 (open triangle), and Y-50049–YXI–SUT4 (open square). Performance of strain Y-50049 without YXI background (star), was evaluated compared with its transformant derivatives Y-50049–XUT4 (cross) and Y-50049–XUT6 (plus). Symbol values are means of two replications while error bars represent the range. The growth plots of Y-50049 (star), Y-50049+XUT4 (cross), and Y-50049+XUT6 (plus) are overlapping since none of the three grew. As a result only the cross symbol can be distinguished since it is on top of the other two. FIG. 7B depicts a graph of the same strains under the same conditions as FIG. 7A and xylose consumption by said strains over time (hours).

FIG. 8A depicts a graph cell growth density of various yeast strains over time (hours) on YP medium supplemented with 24.3 g/L D-glucose and 32.5 g/L D-xylose under oxygen-limited conditions. S. cerevisiae Y-50049–YXI is labeled with a filled circle, Y-50049–YXI–XUT4 with a filled triangle, Y-50049–YXI–XUT5 with a filled diamond, Y-50049–YXI–XUT6 with a filled square, Y-50049–YXI–XUT7 with an open circle, Y-50049–YXI–RGT2 with an open triangle, and Y-50049–YXI–SUT4 with an open square. FIG. 8B depicts a graph of the same strains under the same conditions as FIG. 8A and consumption of xylose as depicted by solid lines or glucose by dotted lines for each strain.

BRIEF DESCRIPTION OF THE SEQUENCES

Figure 1:
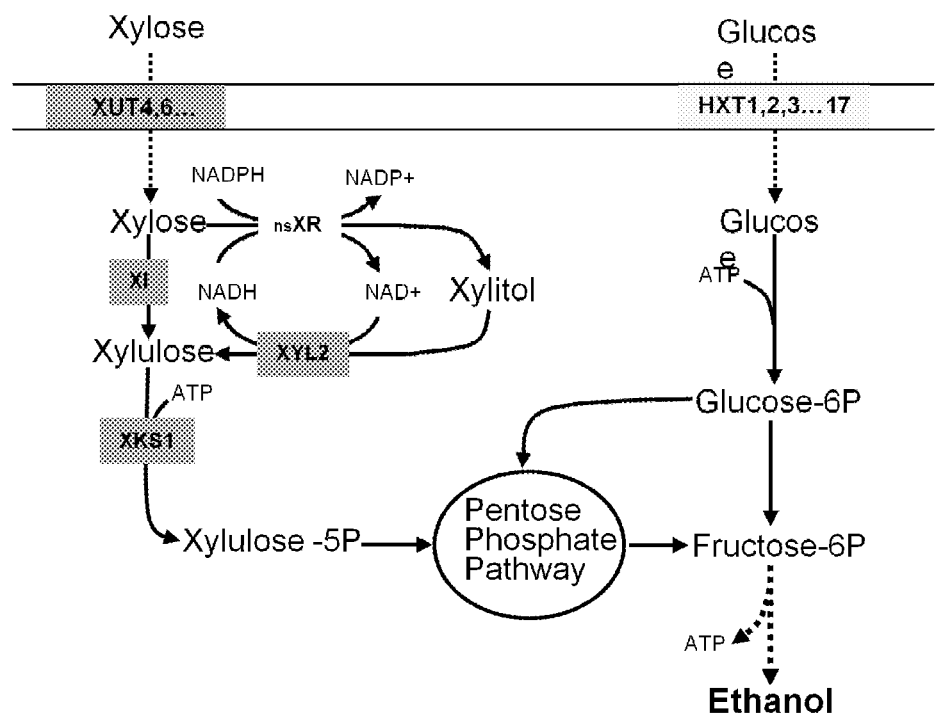
FIG. 1 is a metabolic pathways for mixed sugar fermentation for ethanol production. Xylose transport related genes (XUT4 and XUT6) from *S. stipitis* are incorporated into an inhibitor-tolerant ethanologenic yeast for improved xylose uptake and utilization; a synthesized xylose isomerase gene (YXI) based on codon preference of *S. cerevisiae* is integrated into a defined chromosomal locus as a main xylose utilization route; xylulokinase gene (XKS1) and xylitol dehydrogenase gene (XYL2) from *S. stipitis* are introduced into the yeast strain for enhanced downstream metabolism and xylitol conversion. Non-specific xylose reduction activities by aldose reductase are marked by nsXR in distinguishing from specific xylose reductase (XR) from *S. stipitis*.

Below is a list of primers used with endonuclease restriction sites underlined and italicized as necessary.

```
SEQ. ID. NO. 1:
GCCCGCGGATGAAAAATTACTTTCCAAATG is primer XylA_F.

SEQ. ID. NO. 2:
GCCCGCGGTTATCTAAATAAAATATTATTTACG is primer XylA_R.

SEQ. ID. NO. 3:
GCGCGCATGCATATGAAGAACTACTTCCCAAACGTTCCAGAAG is primer YXI_L.

SEQ. ID. NO. 4:
GCGCGCCCGCGGTTATCTGAACAAAATGTTGTTAACAATGGTTTCCAA is primer YXI_R.

SEQ. ID. NO. 5:
TTTTAGACAATGATTTCAGCTGGAGGAGCC is primer XUT4_L.

SEQ. ID. NO. 6:
GCGCGCAAGCTTTATTCCATCTCATTCAACTTGTACTTAAA is primer XUT4_R.

SEQ. ID. NO. 7:
GCGCGCACTAGTATGTCCAGTGTTGAAAAAAGTGCT is primer XUT6_L.

SEQ. ID. NO. 8:
GCGCGCCCCGGGTTAGCTGATGTTTTCGACATGCTC is primer XUT6_R.

SEQ. ID. NO. 9:
GCAAGCTTATGACCACTACCCCATTTGATGCTCCA is primer XKS1_L.

SEQ. ID. NO. 10:
GCTTAATTAAATTTTAGTGTTTCAATTCACTTTCCATCTT is primer XKS1_R.

SEQ. ID. NO. 11:
GCGAATTCATGACTGCTAACCCTTCCTTGGTGTTGAA is primer XYL2_L.

SEQ. ID. NO. 12:
CCGCGGCCGCTTACTCAGGGCCGTCAATGAGACACTT is primer XYL2_R.
```

-continued

SEQ. ID. NO. 13:
GTTGCGTC*ACTAGT*TGCATTATGGACTTCCTC is primer ADH1_pL.

SEQ. ID. NO. 14:
CTTCAA*CCGCGG*ATAGGCCATCAGGATAGACATA*ATGCAT*TGAGATAGTT is primer ADH1_pR.

SEQ. ID. NO. 15:
GATGGCCTTT*CCGCGG*TTGAAGAA is primer CYC1_tL.

SEQ. ID. NO. 16:
GGAAGCGAT*GTTAAC*AGCGACGAT is primer CYC1_tR.

SEQ. ID. NO. 17:
GCGCGC*GGTACC*CGACGGCTCACAGGTTTTGTAACAAG is primer PGK_pL.

SEQ. ID. NO. 18:
GCGCGC*CTCGAG*TGTTTTATATTTGTTGTAAAAAGTAGATAATTACTTCCTTGATG is primer PGK_pR.

SEQ. ID. NO. 19:
GCGCGC*CCGCGG*ATTGAATTGAATTGAAATCGATAGATCAATTTT is primer PGK_tL.

SEQ. ID. NO. 20:
GCGCGC*GAGCTC*TTCAAGCTTACACAACACGGTTTATTT is primer PGK_tR.

SEQ. ID. NO. 21:
GC*CAGCTG*AACACACCCCGCGTTTATTTACCTA is primer PDC1_pL.

SEQ. ID. NO. 22:
GC*AAGCTT* *GAGCTC*TGATTTGACTGTGTTATTTTGCGTGA is primer PDC1_pR.

SEQ. ID. NO. 23:
GC*AAGCTT*CA*TTAATTAA*ATTGAAATCATGTTGCCAGTCTT is primer PDC1_tL.

SEQ. ID. NO. 24:
GC*GGTACC*AACCATTATTTGTATCGAGGTGTCTA is primer PDC1_tR.

SEQ. ID. NO. 25:
GC*GGTACC*TGAGCCGATCTAAATACTTCTGTGTT is primer TDH2_pL.

SEQ. ID. NO. 26:
GC*GAATTC*TTTGTTTTGTTTGTTTGTGTGATGA is primer TDH2_pR.

SEQ. ID. NO. 27:
CC*GCGGCCGC*ACTCCTTAAGTTACTTTAATGATTTAGTTTTT is primer TDH2_tL.

SEQ. ID. NO. 28:
GC*CTCGAG*GCGAAAAGCCAATTAGTGTGAT is primer TDH2_tR.

SEQ. ID. NO. 29:
GC*CTGCAG*AGGTGCCGGTGTCGTTGTCG is primer ADH2-1a_F.

SEQ. ID. NO. 30:
GC*GTCGAC*CAGCGTCAGCGGTAGCGTATTCTT is primer ADH2-1a_R.

SEQ. ID. NO. 31:
GC*GTTAAC*GCGCGGTGCCCACGGTATCATC is primer ADH2-2_F.

SEQ. ID. NO. 32:
GGA*AGCGGAAGAGC*GTTCCCCACGTAAGAGCCGACAAT is primer ADH2-2a_R.

SEQ. ID. NO. 33:
AACATTACCGACCCAATGGA is primer qYXIp_L.

SEQ. ID. NO. 34:
CACCTTCTGGAGCAATGTCA is primer qYXIp_R.

SEQ. ID. NO. 35:
CGAAGGTGACATTGCCTCTT is primer qXKS1_L.

SEQ. ID. NO. 36:
AGCCAAAGGCAACGAGATAA is primer qXKS1_R.

SEQ. ID. NO. 37:
GATCAAGGCTTTCGGTGGTA is primer qXYL2_L.

SEQ. ID. NO. 38:
ACCGACTTGAACGAAACGAC is primer qXYL2_R.

SEQ. ID. NO. 39:
TAGGTGACATCGTTGGCAGA is primer qXUT4_L.

-continued

SEQ. ID. NO. 40:
GCAATACCGGCAATCAATCT is primer qXUT4_R.

SEQ. ID. NO. 41:
GCTCTTGTCATGGCTGGTTT is primer qXUT6_L.

SEQ. ID. NO. 42:
AGACGCCGAAGAATGAGTTG is primer qXUT6_R.

SEQ. ID. NO. 43:
GCGCGCCTGCAGATGTCTTCGTTATTGACTAACGAATACTTC is primer XUT4_P_L.

SEQ. ID. NO. 44:
GCGCGCAAGCTTTTATTCCATCTCATTCAACTTGTACTTAAA is primer XUT4_H_R.

SEQ. ID. NO. 45:
GCGCGCCTGCAGATGTCCAGTGTTGAAAAAAGTGCT is primer XUT6_P_L.

SEQ. ID. NO. 46:
GCGCGCCCCGGGTTAGCTGATGTTTTCGACATGCTC is primer XUT6_Sm_R.

SEQ. ID. NO. 47:
GCGCGCCTCGAGATGTCTTCGTTATTGACTAACGAATACTTC is primer XUT4_X_L.

SEQ. ID. NO. 48:
GCGCGCCCGCGGTTATTCCATCTCATTCAACTTGTACTTAAA is primer XUT4_S_R.

SEQ. ID. NO. 49:
GCGCGCGTCGACATGACGGAAAGAAGCATTGG is primer XUT5_S_L.

SEQ. ID. NO. 50:
GCGCGCGATATCTTACTTCTTTGTATTAACAACAAAACCTTG is primer XUT5_EV_R.

SEQ. ID. NO. 51:
GCGCGCCCCGGGATGTCCAGTGTTGAAAAAAGTGCT is primer XUT6_Sm_L.

SEQ. ID. NO. 52:
GCGCGCACTAGTTTAGCTGATGTTTTCGACATGCTC is primer XUT6_S_R.

SEQ. ID. NO. 53:
GCGCGCGTCGACATGACTTTTGCAGTTAACTTGTATGTG is primer XUT7_S_L.

SEQ. ID. NO. 54:
GCGCGCGGATCCTTAGTCCAAATCGTCCAAATCGTC is primer XUT7_B_R.

SEQ. ID. NO. 55:
GCGCGCGTCGACATGGGTTTAGAAGACAGTGCTCTC is primer RGT2_S_L.

SEQ. ID. NO. 56:
GCGCGCGATATCCTATACAGAAGCTTCTTCAACTTCAGA is primer RGT2_EV_R.

SEQ. ID. NO. 57:
GCGCGCGTCGACATGTCCTCACAAGATTTACCCTCG is primer SUT4_S_L.

SEQ. ID. NO. 58:
GCGCGCGGATCCCTAAACTTGCTCTTGCTCTTTTGTTTC is primer SUT4_B_R.

SEQ. ID. NO. 59:
GCGCGCGGTACCCGACGGCTCACAGGTTTTGTAACAAG is primer PGK_PL.

SEQ. ID. NO. 60:
GCGCGCCTCGAGTGTTTTATATTTGTTGTAAAAAGTAGATAATTATTCCTTGATG is primer PGK_PR.

SEQ. ID. NO. 61:
GCGCGCCCGCGGATTGAATTGAATTGAAATCGATAGATCAATTTT is primer PGK_TL.

SEQ. ID. NO. 62:
GCGCGCGAGCTCTTCAAGCTTACACAACACGGTTTATTT is primer PGK_TR.

SEQ. ID. NO. 63:
atgaagaactacttcccaaacgttccagaagttaagtacgaaggtccaaactctaccaacccattcgctttcaagtactacgacgctaacaag gttgttgctggtaagaccatgaaggaacactgtagattcgctttgtcttggtggcacaccttgtgtgctggtggtgctgacccattcggtgttac caccatggacagaacctacggtaacattaccgacccaatggaattggctaaggctaaggttgacgctggtttcgaattgatgaccaagttgg gtattgaattcttctgtttccacgacgctgacattgctccagaaggtgacaccttcgaagaatctaagaagaacttgttcgaaattgttgactaca ttaaggaaaagatggaccaaaccggtattaagttgttgtggggtaccgctaacaacttctctcacccaagattcatgcacggtgcttctacctct tgtaacgctgacgttttcgcttacgctgctgctaagattaagaacgctttggacgctaccattaagttgggtggtaagggttacgttttctctgggt ggtagagaaggttacgaaaccttgttgaacaccgacttgggtttggaattggacaacatggctagattgatgaagatggctgttgaatacggt agagctaacggtttcgacggtgacttctacattgaaccaaagccaaaggaaccaaccaagcaccaatacgacttcgacaccgctaccgtttt ggctttcttgagaaagtacggtttggaaaaggacttcaagatgaacattgaagctaaccacgctaccttggctggtcacaccttcgaacacga attggctatggctagagttaacggtgcttcggttctgttgacgctaaccaaggtgacccaaacttgggttgggacaccgaccaattcccaac cgacgttcactctgctaccttggctatgttggaagttttgaaggctggtggtttcaccaacggtggtttgaacttcgacgctaaggttagaagag gttctttcgaattcgacgacattgcttacggttacattgctggtatggacaccttcgctttgggtttgattaaggctgctgaaattattgacgacgg tagaattgctaagttcgttgacgacagatacgcttcttacaagaccggtattggtaaggctattgttgacggtaccacctctttggaagaattgg aacaatacgttttgacccactctgaaccagttatgcaatctggtagacaagaagttttggaaaccattgttaacaacattttgttcagataa is the cDNA of the gene YXI.

SEQ. ID. NO. 64:
attatctacttttacacaaatataaaacactcgaggtcgacatgggtttagaagacagtgctctcttgcaaaagtacatcaacttcggtgaaaa gaaggctggttccaccaccatgggtatctgtgttggtttgttcgcagccttcggtggtatccttttcggttatgacactggtaccatctccggtat catggccatggactacgtcactgccagattcccatccaaccaccaatctttcagttcttctgaatcttcccttattgtttccattttgtctgttggtac cttctttggttctctttctgcatctttcatctccgacagattgggtcgtagattgactttaatgatctccaccttgatcatcttcaatgtcggtattatctt gcaaactgcctctactagcattccacttttgtgtgttggtagagttttttgctggtcttggtgttggtctcatttccgctgttattccattgtaccaagct gaaacagttccaaagtggatcagaggtgctgttgtctcctgttaccaatgggccattacccttggtttgttgttggctgctgttgttaaccaaggt acccacaacagaaatgactctggttcctacagaatcccaattgctatccaattcttgtgggctttgattttgggaggtggtatgtgtttgttgcca gaaaccccaagattctgggtttctaaaggtgacaacgacagagccaaggactccttgagaagattgagaaagttgcccctcgaccatcccg acttgattgaagaatacgaagaaatcaaggctaactacgaatacgaagctcaatacggttcaggttcttggagtcaagttttttgctaacaagaa ccaccaaagaaagagattggccatgggtgttggtatccaagccttgcaacaattgaccggtattaactttatcttctactatggtactaacttctt caaggggttctggtatcaaaaacgaattccttatccaaatggccactaacattgtcaacttcggttctactgtcccaggtattcttttggttgaaatta ttggtagaagaaagttgttgttgggtggttctgcagttatgtccatttctcaattgattgttgctattgtcggtgttgccgctggtgaaggttcaactt ctgccaacaagtgtttggttgccttcgtttgtatcttcattgctgctttcgcagccacttggggtcctcttttgttgggctgtcattgccgaatgttacc cacttacagttagacaaaagtccatctccttgtgtacagcttccaactggttgtggaactggggtattgcctacgctactccttacatggtcaact ccggtccaggtaacgccaacttgggttccaaggttttcttcatctggggtggttgtaatatcattggtggtcttttcgtgtggtaccttgtctacga aactaagggcttgaccttagaacaaatcgatgaaatgtacgaaaaggttccaaaggcttggcaatctaccagattcattccatccgaacatgc attcactcaaccatccgcagctgcctctgtctcttctggtaaggctgaaggtgtttctgaagttgaagaagcttctgtataggatatcgaattcct gcagcccggggggatccactagttctagagcggccgccaccgcggatg is the cDNA of the xylose transporter gene

RGT2.

SEQ. ID. NO. 65:
tatctactttttcaacaaatataaaacactcgaggtcgacatgacttttgcagttaacttgtatgtgtttgcagttggtagagtgctttctggggtgg gtgtaggagttctatcgactatggtgccgtcctatcaatgcgaaattagtcccagcgaagaaagaggcaagttggtgtgtggagagttcacg ggaaatatcactggttatgctctcagtgtatgggccgattacttctgctactttattcaagatataggtgatgcaagggagaagcctcatagcttc tttgcccacttgtcctggcgattgcctctattcatccaggtggtgatagcggctgttctcttgttggggggatttttttattgtcgagtcacctcgttgg ttattagatgtagaccaggaccaacaaggattccatgtattagcgttgctctatgattcacatctagatgataacaaaccacgtgaagagttctttt atgatcaagaactccatctcttgttagaaagagaaactacacctaagagcgaacgaacttggaaacatatgttcaagaactacatgacccgagt gcttatagcttgttcagcacttggctttgcacagttcaacggcataaatatcatttcgtactatgcccccatggtatttgaagaagcaggcttcaa caactccaaggctttacttatgacaggcatcaactctatagtatattggttcagtacgattcctccgtggtttctcgtggatcattggggtagaaa gccaattttgatatccggggtttatctatgggaatatgtattggtttgattgcggtggtaattctactagacaagtcgttcacaccgtctatggttg cggtgttggtgataatctacaatgcatcttttggctacagttgggggtcctatcggattcttgatcccgccggaggtgatgccattggcagttaga tcgaaaggtgtttctatttctacggctacaaactggtttgccaattttgttgtgggtcagatgacgccaattctacagcagagattgggctgggg -continued aacttatctattcccggctggtagttgtatcatctcggtgatagtggtgattttcttctatccagagacaaagggtgtagagctagaggatatgga ctctgtgttcgagagcttttacaactacaagtctccgttcaagatttcacgaaagagacaccagaatgatggccaggcgtaccaaagggtag agaacgatatccgccacaacgatgtagaaatggacgatttggacgatttggactaaggatccactagttctagagcggccgccaccgcgga tgaattgaatgaaa is the cDNA of the xylose transporter gene XUT7.

SEQ. ID. NO. 66:
acttttcacaaatataaaacactcgaggtcgacatgacggaaagaagcattggacctttaatccccagaaataagcacttattctatggatcc gtattatagatgagtattgttcacccaactatcatgggatacgattccatgatggttggtagtattcttaatctagatgcatatgtaaattatttccac ttaacggctgctaccactggactcaatactgctgcagtatggcttgggcaagtaattgccacattgacagttattctgtatttcaatgacaaattt ggtagaagaagctcagtttgtataagtattgcaatcagtttggttggggttgcattgcaatcagcagcccagaacattgagatgtttattatcgg aagaatagttattggttttggaatatctattggttttgtctcatctaccatttggtaagtgaactagcccctccagacaaaagaggatttattcttgg attgagttttacaagctttctagtaggaagtttaattgcagcaggtgtcacatatggaacaagaaatgctcctggagactggtgttggagaatcc catcaattattcaaggggctccagatattgttgctattattaacatactctttatttcagaatcaccaaggtggttgattgcaaaggaaagattcag cgaagctcgtgaaattatttctatcattagtgatgttcctattgaagatgcacatgaagaatgtgaaaagatacatgcccatattcaaactgagaa gactgctttccctggcaataagtggaaacaaatggtgagctccaagagcaatacaagaagagttattatcttgttcacacaggccatagttact gaaatggccggttcttcagttggatcgtactatttttcaattatattaactcaagctggggtcaaagattcgaatgatagactaagagtaaatattg tgatgagttcgtggtcattggtaattgctctttccggatgtctaatgtttgacagaattggaagaaagatgcaatcgctcatttcgttatcaggtat gatcatatgctttatagttttaggtgttttggttaaagaatatggcgatggtcatagcaagagcggaagttacgcagctgtcgccatgatgttttta ttcacaggatttttactcattcactttcactccattgaactctttgtaccctccagaattgttccctacgtgttgagaagtacaggagttacactcttt aatattttcaacggctgctggggacttttcgcaagtttcattttacccattgcaatgaatggaattggctggaaattttacatcattaatgcttgctat gacgtcatattccttccaataataatgttctgttggattgagacaaagggaattaatttggatacaattagtgaagtattgcacggaagaggacc tgaagatgaagaaagcattgaagaaagtcacagcctaatcagacaaggttttgttgttaatacaaagaagtaagatatcgaattcctgcagcc cgggggatccactagttctagagcggccgccaccgcggatgaatgaatgaaat is the cDNA of the xylose transporter gene XUT5.

SEQ. ID. NO. 67:
tctggaatggcgggaaagggtttagtaccacatgctatgatgcccactgtgatctccagagcaaagttcgttcgatcgtactgttactctctctc tttcaaacagaattgtccgaatcgtgtgacaacaacagcctgttctcacacactcttttcttctaaccaaggggtggtttagtttagtagaacct cgtgaaacttacatttacatatatataaacttgcataaattggtcaatgcaagaaatacatatttggtcttttctaattcttagtttttcaagttcttagat gctttcttttctcttttttacagatcatcaaggaagtaattatctacttttttacacaaatataaaacactcgagatgtccagtgttgaaaaagtgct gaaactgcttcctatacgtcgcaggtcagcgcaagcggctctgcaaagaccaacagctaccttggcctcagaggcaacaaacttaattttgc tgtctcttgttttgctggtgttggtttcttacttttgggttacgatcaaggtgtcatgggttcattgttgaccttgccatccttcgaaaacactttcccg gccatgaaggctagcaacaacgctaccttacaaggcgccgttattgcactttatgaaatcggttgtatgtcttcttcttagcaaccatttaccttg gtgacagattgggtagattgaagatcatgtttattggctgtgtaattgtctgtattggtgctgctttgcaagcttctgcttcactattgctcacttga ctgttgctagaattatcactggtttaggtacaggtttcatcacttctactgttccagtttaccaatcggagtgctctccagccaagaaaagaggac agttgatcatgatggaaggttctcttatcgcccttggcattgccatctcatactggattgactttggatttacttttttgagaaacgatggtttgcact cctcggcttcttggagagcacctatcgcgcttcaatgtgtcttcgctgtcttgttgatttccacagtcttcttcttcccagaatctccaagatggttg ctcaacaaaggtaggaccgaagaagctagagaagttttttctgctctttacgacttgccagccgactctgaaaagatttctattcaaattgaaga aattcaagctgctatagatttagaaagacaagccggagaaggtttcgtacttaaggaattgttcactcagggcccagccagaaacttgcagc gtgtggccttgtcatgttggtctcaaataatgcaacaaatcactggtattaacattattacgtactatgctggtactattttttgaatcatacattggta tgagtccatttatgtcaagaatcttggctgccttgaacggtactgaatatttccttgtctctcttattgcttttctacaccgtcgaaagattaggtaga agattccttttgttctgggtgccatcgccatggcttcttgtcatggctggtttaactgttaccgttaaacttgccggtgaaggcaacacccatgct ggtgtcggtgctgctgttcttttgtttgcattcaactcattcttcggcgtctcctggttaggtggatcctggttgttaccacctgaattgttgtctttga aattgagagctcctggtgctgctttgtcgaccgcttctaactgggcttttaacttcatggttgtcatgatcactcctgtcggtttccaaagtattggt -continued tcctacacctaccttatctttgctgccatcaatttgttgatggctccggtcatctacttcttgtatcccgaaaccaagggtagatcgttggaagaaa
tggatatcattttcaaccaatgtcctgtttgggagccatggaaggttgtccaaattgccagagacctccctattatgcactcagaagttcttgacc
acgaaaaggatgtcattattgaaaaatctagaatagagcatgtcgaaaacatcagctaaactagttctagagcggccgccaccgcggatga
atgaatgaaatc is the cDNA of the xylose transporter gene XUT6.

SEQ. ID. NO. 68:
cacaaatataaaacactcgagatgtcttcgttattgactaacgaatacttcaaagactactaccacaacccgactcctgttgaagtgggtactat
gattgctatcttagagatcggcgcacttttttcctccttcatagctggaagagtaggtgacatcgttggcagaagaagaaccattagatacggg
tctttcattttgtgtagtaggcggtcttgtacaagctacttcggtcaatattgtcaatctctcactaggaagattgattgccggtattgccattggcttt
tgacaaccatcatcccatgctaccagtctgaaatcagcccccagacgatagaggtttctatgcctgtttggagttcaccggaaatatcattgg
atatgctagtagtatttgggtagactacgggttttcattttagacaatgatttcagctggaggagcccattgtatgttcaggttgttattggctcca
tgttatttattggttcattccttattgtagaaacccctagatggctcttggatcacaaccatgatatcgaaggcatgattgtcatttctgacttgtatg
cagatggtgatgtggaagacgatgatgctattgctgagtacagaaacataaaggaaagtgtcttgatagccagagttgaaggcggagagag
atcgtaccagtatttgttcaccaaatataccaagagacttttctgtggcatgcttttcgcaaatgtttgcccagatgaatggtataaacatggtatct
tactatgctcctatgatcttcgaatctgctggctgggttggtagacaagctatcttgatgactggtatcaactccattatctacatctttagtaccatt
cctccatggtacttagttgattcttggggcagaaaacctttgcttttatctggatctgtgctcatgggtgttccgctcttaaccattgcttgttcgttat
tcttaaacaacacatacacacccggggttgtggttggcagtgtaatcgtattcaatgctgcttttggatacagttggggtccaattccttggctca
tgagcgaagtgttccctaactcagttagatcaaaaggtgctgccatgtctactgcaaccaactggctctttaactttattgttggagagatgaca
cctattttgttggatacaattacctggagaacttacttgatcccggcaacttcgtgtgtattatcgtttttttgctgttggattttttatttccagagacca
agggtttagcattggaggatatgggctccgtattcgatgataattcgtcaatattttcatatcactcaactccttccactgggtatggtgcgaccg
agtctaacagtaatgccaggagagcaagtgtcatctcttcagaaaactaccaggatagtttgcatcagacagcggcttcattggctaggaatc
cttcaagcatgaggcctgattacgatggcataatcacaggagctgctacccttttcgccagtaccaccattaaaaccaataaagtctgatgcgt
cagtccattcagtcgatgccataattccaagcatttccagcaatattccgcaggaaattgaaccaccaacctttgatgaagtctttaagtacaag
ttgaatgagatggaataaccgcggatgaatgaatgaaat is the cDNA of the xylose transporter gene XUT4.

SEQ. ID. NO. 69:
tatctacttttttacacaaatataaaacactcgaggtcgacatgtcctcacaagatttaccctcgggtgctcaaaccccaatcgatggttcttccat
cctcgaagataaagttgagcaaagttcgtcaaatagccaacgtgatttagcttctattccagcaacagatatcaaagcctatctcttggtttgttt
cttctgcatgttggttgccttcggtggcttcgtattcggtttcgataccggtactatttccggtttccttaatatgtctgatttcctttccagatttggtc
aagatggttctgaaggaaaatatttgtccgatatcagggttggtttgattgtttccatttttaacattggttgtgcaattggtggtattttcctttctaa
gataggagatgtttacggtagaagaattggtatcatttcagctatggttgtctatgtcgtcggtataatcatccagatctcgtcccaagacaagtg
gtatcaacttacaattggacgtggagttacaggattagctgttggtactgtttcggttttgtctccaatgttcattagtgaaagtgctccaaagcatt
tgagaggtactttggtatactgttaccaattatgcatcaccttaggtatttttcattggttactgtgtcacttatggaaccaaagatttaaatgattcaa
gacaatggagagttccctttgggtttatgtttcctctgggctattttcttagttgtcggtatgttggctatgcctgaatcccaagattcttaattgaaa
agaagagaatcgaagaagccaagaagtcccttgcaagatccaacaagttatctccagaagatccaggtgtctacactgaagttcaattgatt
caggctggtattgacagagaagctgctgcaggttctgcttcatggatggaattgatcactggtaagccagctattttcagaagagttatcatgg
gaatatcttacagtctttgcaacaattaactggtgtcaactatttcttctattacggaactacaatcttccaagctgttggtttgcaagattccttcc
agacttccatcatcttaggtacagtcaactttctttctacatttgttggtatttgggccattgaaagatttggaagaagacaatgtttgttagtcggtt
ctgctggtatgttcgtttgtttcatcatttactctgtcattggtacaactcatttgttcattgatggagtagtagataacgacaacacccgtcaactgt
ctggtaatgctatgatctttatcacttgtttgttcatcttcttctttgcctgtacttgggctggaggtgttttttacaatcatttccgaatcatatccattga
gaatcagatccaaggctatgtctattgccactgccgctaactggatgtggggtttcttgattcattctgcactccattcattgttaacgccatcaa
cttcaagttcggctttgtgtttactggttgtttgctcttttcgttcttctatgtctacttctttgtcagcgaaacaaaggtttgtcgttggaagaagttg
atgagttgtacgctgagggaattgcaccatggaaatccggtcatgggttcctccttctgcacaacaacaaatgcaaaactctacttatggtgc -continued

```
cgaaacaaaagagcaagagcaagtttagggatccactagttctagagcggccgccaccgcggatgaatgaatgaaatcg is the
cDNA of the xylose transporter gene SUT4.
```

Deposit of Biological Material

Strain NRRL Y-50463 was deposited on Jan. 24, 2011, under the provisions of the Budapest Treaty in the Agricultural Research Culture Collection (NRRL) in Peoria, Ill., and has been assigned Accession No. NRRL Y-50463.

Strain NRRL Y-50465 was deposited on Feb. 6, 2011, under the provisions of the Budapest Treaty in the Agricultural Research Culture Collection (NRRL) in Peoria, Ill., and has been assigned Accession No. NRRL Y-50465 and is also referred to as Y-50049–YXI–RGT2.

Strain NRRL Y-50466 was deposited on Feb. 6, 2011, under the provisions of the Budapest Treaty in the Agricultural Research Culture Collection (NRRL) in Peoria, Ill., and has been assigned Accession No. NRRL Y-50466 and is also referred to as Y-50049–YXI–XUT7.

Strain NRRL Y-50746 was deposited on May 4, 2012, under the provisions of the Budapest Treaty in the Agricultural Research Culture Collection (NRRL) in Peoria, Ill., and has been assigned Accession No. NRRL Y-50746 and is also referred to as Y-50049–YXI–XUT5.

Strain NRRL Y-50747 was deposited on May 4, 2012, under the provisions of the Budapest Treaty in the Agricultural Research Culture Collection (NRRL) in Peoria, Ill., and has been assigned Accession No. NRRL Y-50747 and is also referred to as Y-50049–YXI–XUT4.

Strain NRRL Y-50748 was deposited on May 4, 2012, under the provisions of the Budapest Treaty in the Agricultural Research Culture Collection (NRRL) in Peoria, Ill., and has been assigned Accession No. NRRL Y-50748 and is also referred to as Y-50049–YXI–SUT4.

Strain NRRL Y-50749 was deposited on May 4, 2012, under the provisions of the Budapest Treaty in the Agricultural Research Culture Collection (NRRL) in Peoria, Ill., and has been assigned Accession No. NRRL Y-50749 and is also referred to as Y-50049–YXI–XUT6.

The subject cultures have been deposited under conditions that assure that access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., the culture will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposits will be irrevocably removed upon the granting of a patent disclosing them.

DETAILED DESCRIPTION OF THE INVENTION

Definitions

As used in the specification and claims, the singular form "a", "an", and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences.

Methods which are well known to those skilled in the art may be used to construct expression vectors containing sequences encoding xylose isomerase gene YXI, Xylulokinase gene (XKS1_ps), xylitol dehydrogenase gene (XYL2_ps), xylose transport related genes (XUT4_ps, XUT6_ps, XUT5_ps, XUT6_ps, XUT7_ps, RGT2, SUT4) and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y. and Ausubel, F. M. et al. (1989) Current Protocols in Molecular Biology, John Wiley & Sons, New York, N.Y., and incorporated herein by reference.

Preferably in the present invention, YXI (xylose isomerase), XKS (xylulokinase), XYL (xylitol dehydrogenase) and at least one XUT (xylose transporter gene) are constitutively expressed. For example, after introduction of the YXI gene into a chromosomal integration-type vector or the like, the vector is integrated into a yeast chromosome, and then single or several copies of the genes are preferably expressed. These genes may be integrated by homologous recombination into a single allele of a chromosomal DNA. Alternatively, the gene may be separately integrated by homologous recombination into different alleles of a chromosomal DNA. Preferably, the five types of enzyme gene are simultaneously integrated into a single allele of a host DNA. Techniques for chromosomal integration of plasmid DNA by homologous recombination are well known in the art, as reported in Casey, et al., (1991), American Society of Microbiology, Vol. 57, No. 9, 2677-2682, and incorporated herein by reference. Following chromosomal integration of a synthesized YXI, genes for XKS, XYL and at least one XUT were plasmid carrier. As detailed below, in a preferable embodiment, a yeast strain would comprise a chromosomal integration of YXI along with a xylose transporter gene XUT4, XUT5, XUT6, XUT7, RGT2 or SUT4.

In addition to *S. cerevisiae*, it is envisioned that other yeast species could be used to obtain yeast strains according to the invention for use in the methods of the invention. Other suitable yeast species include, without limitation, *Candida boidinii*, *Enteroramus dimorphus*, *Candida jeffriesii*, *Debaryomyces hansenii*, *Candida Guillermondii*, *Candida shehatae*, *Brettanomyces naardensis*, *Candida guillermondii*, *Candida lyxosophilia*, *Candida intermedia*, *Candida tenuis*, *Hansenula polymorpha*, *Kluyveromyces marxianus*, *Kluyveromyces lactis*, *Kluyveromyces fragilis*, *Kluyveromyces thermotolerans*, *Pachysolen tannophilus*, *Pichia Segobiensis*, and *Spathaspora passalidarum*.

In another aspect, the present invention provides a method of fermenting xylose in a xylose-containing material to produce ethanol using the yeast of the invention as a biocatalyst. Another aspect of the present invention provides a method of fermenting xylose in a xylose-containing material to produce xylitol as a byproducts. Ideally the invention aims to minimize producing the byproduct of xylitol. In this embodiment, the yeast preferably has reduced xylitol dehydrogenase activity such that xylitol is accumulated. Preferably, the yeast is recovered after the xylose in the medium is fermented to ethanol and used in subsequent fermentations.

By "xylose-containing material" it is meant any medium comprising xylose, whether liquid or solid. Suitable xylose-containing materials include, but are not limited to, hydrolysates of polysaccharide or lignocellulosic biomass such as corn hulls, wood, paper, agricultural by-products, and the like.

By a "hydrolysate" as used herein, it is meant a polysaccharide that has been depolymerized through the addition of water to form mono and oligosaccharides. Hydrolysates may be produced by enzymatic or acid hydrolysis of the polysaccharide-containing material, by a combination of enzymatic and acid hydrolysis, or by another suitable means.

Preferably, the yeast strain is able to grow under conditions similar to those found in industrial sources of xylose. The method of the present invention would be most economical when the xylose-containing material can be inoculated with the mutant yeast without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. Serially subculturing yeast selects for strains that are better able to grow in the presence of sulfite or phenolic inhibitors.

It is expected that yeast strains of the present invention may be further manipulated to achieve other desirable characteristics, or even higher specific ethanol yields. For example, selection of mutant yeast strains by serially cultivating the mutant yeast strains of the present invention on medium containing hydrolysate may result in improved yeast with enhanced fermentation rates.

Strains and Media

Strains of *S. cerevisiae, S. stipitis*, and *Escherichia coli* used are listed in Table 1. Yeast strains were maintained and aerobic growth was measured on YP medium (1% yeast extract, 2% peptone) supplemented with 20 g l$^{-1}$ D-glucose or 20 g l$^{-1}$ D-xylose as carbon source. G418 or hygromycin B was added into medium for selection and maintaining positive transformants as previously described in Taxis C, Knop M (2006), Biotechniques 40:73-78 and hereby incorporated by reference. A YP medium amended with 50 g l$^{-1}$ D-xylose was used for evolutionary adaptation, growth assay and ethanol fermentation; and with 50 g l$^{-1}$ D-xylose and D-glucose each was used for growth test and co-fermentation assay. Inhibitors of furfural and HMF were added into a medium for evaluation of cell growth under the inhibitor challenge. Competent cells of *E. coli* were grown on LB medium (1% tryptone, 0.5% yeast extract, 1% NaCl, pH 7.0; 20 g l$^{-1}$ agar was added for solid medium) amended with 100 mg l$^{-1}$ ampicillin for plasmid selection.

TABLE 1

Plasmids and strains used

| ID | Description | Reference |
|---|---|---|
| Plasmids | | |
| pUG6 | loxP-KanMX-loxP cassette | Güldener et al. (1996) |
| pYES2 | Yeast protein expression vector | Invitrogen Carlsbad, CA |
| pRS42H | System integrative vector | Taxis and Knop (2006) |
| pUG-ADH1_p-CYC1_t | pUG6 with ADH1 promoter and CYC1 terminator | This study |
| pUG-ADH1_p-ADH2 | pUG6 with ADH1 promoter, CYC1 terminator and ADH2 integration fragments | This study |
| pUG-ADH1_p-XylA | pUG6 with XylA inserted between ADH1 promoter and CYC1 terminator | This study |
| pUG-ADH1_p-YXI | pUG6 with YXI$^{sm}$ gene inserted between ADH1 promoter and CYC1 terminator | This study |
| pYES2 + XKS1 | pYES2 with XKS1 gene | This study |
| pYES2 + XKS1 + XYL2 | pYES2 with XKS1 and XYL2 genes | This study |
| pRS42H + XUT4 | pRS42H with XUT4 gene | This study |
| pRS42H + XUT6 | pRS42H with XUT6 gene | This study |
| pRS42H + XUT4 + XUT6 | pRS42H with XUT4 and XUT6 genes | This study |
| pRS42H + XUT4 + XUT6 + XKS1 + XYL2 | pRS42H with XUT4, XUT6, XKS1 and XYL2 genes | This study |
| Strains | | |
| *S. cerevisiae* NRRL Y-50049 | Inhibitor-tolerant derivative of strain NRRL Y-12632 through evolutionary engineering | ARS Culture Collection, Peoria, IL, USA |
| *S. stipitis* NRRL Y-7124 | Wild type of xylose utilizing yeast | ARS Culture Collection, Peoria, IL, USA |
| Y-50049-XylA | Y-50049 with XylA gene from *C. phytofermentans* | This study |
| NRRL Y-50463 | Genetically engineered Y-50049-YXI_F10 with XUT4, XUT6, XKS1, and XYL2 genes | This study |
| *E. coli* Top 10 | Competent cells | Invitrogen Carlsbad, CA |
| *E. coli* DH10B | Competent cells | Invitrogen Carlsbad, CA |

Preparation of Genomic DNA

Yeast genomic DNA was prepared using DNeasy Blood & Tissue Kit (QIAGEN, Alameda, Calif., USA) following manufacturer's instructions. Bacterial DNA was prepared as previously described in Sambrook J, Russell DW (2001) Molecular cloning: A laboratory manual, third ed. Cold Spring Harbor Laboratory Press, Cold Spring Harbor, N.Y. Crude genomic DNA was used as template for PCR amplification. Genomic DNA of *Clostridium phytofermentans* strain ISDg (ATCC 700394) was supplied by American Type Culture Collection (Manassas, Va.) and used for amplification of xylose isomerase gene XylA as control.

Synthesis of Codon-Optimized Xylose Isomerase Gene

Using amino acid sequence of xylose isomerase from *C. phytofermentans*, a codon-optimized xylose isomerase gene (YXI) was designed on principle of highly expressed gene codons of *S. cerevisiae*. A total of 1317 bp nucleotides encoding 438 amino acids were composed. The full length of YXI gene was synthesized by Epoch Biolabs, Inc. (Sugar Land, Tex.) based on individual custom requirements and its sequence was deposited at NCBI nucleotide database under Accession No. JF261697.

HPLC Analysis

Samples of culture supernatant were taken periodically from 0 to 120 h, and glucose, xylose, ethanol, xylitol, furfural, HMF, furanmethanol (FM) and furan dimethanol (FDM) were measured using a high performance liquid chromatography (HPLC) system of Water (Milford, Mass.) and Shimadzu (Columbia, Md.). The HPLC was equipped with an autosampler controlled at 10° C., a programmable pump, an Aminex HPX-87 H column (Bio-Rad Laboratories, Hercules, Calif.) proceeded by a Microguard cartridge, a Spectra-Physics Spectra 100 variable wavelength UV detector (215 nm), and a refractive index detector. The column was maintained at 65° C., and samples were eluted with 1.6 mM $H_2SO_4$ at 0.6 ml $min^{-1}$ isocratic flow. A standard curve was constructed for each detected chemical and metabolic conversion product for HPLC assays.

EXAMPLE 1

Plasmid Construction

All DNA manipulations were performed using standard molecular biology techniques as described by Sambrook and Russell. *E. coli* Top10 and DH10B (Invitrogen, Carlsbad, Calif., USA) were used for gene cloning. Primers used for plasmid construction are listed in the Description of Sequences above. Plasmids were extracted using QIApre Spin Miniprep Kit (QIAGEN, Alameda, Calif., USA). PCR products were purified using QIAquick PCR Purification Kit (QIAGEN, Alameda, Calif., USA) and QIAquick Gel Extraction Kit (QIAGEN, Alameda, Calif., USA) was used to recover interested DNA fragments from agarose gel. Bacterial transformations were performed using Gene Pulser Xcell Electroporation system (BioRad, Hercules, Calif.), and selection made on LB plate containing 100 mg $l^{-1}$ ampicillin. All constructed plasmids were confirmed by PCR, restriction endonuclease digestion, or DNA sequencing if necessary.

Figure 6:
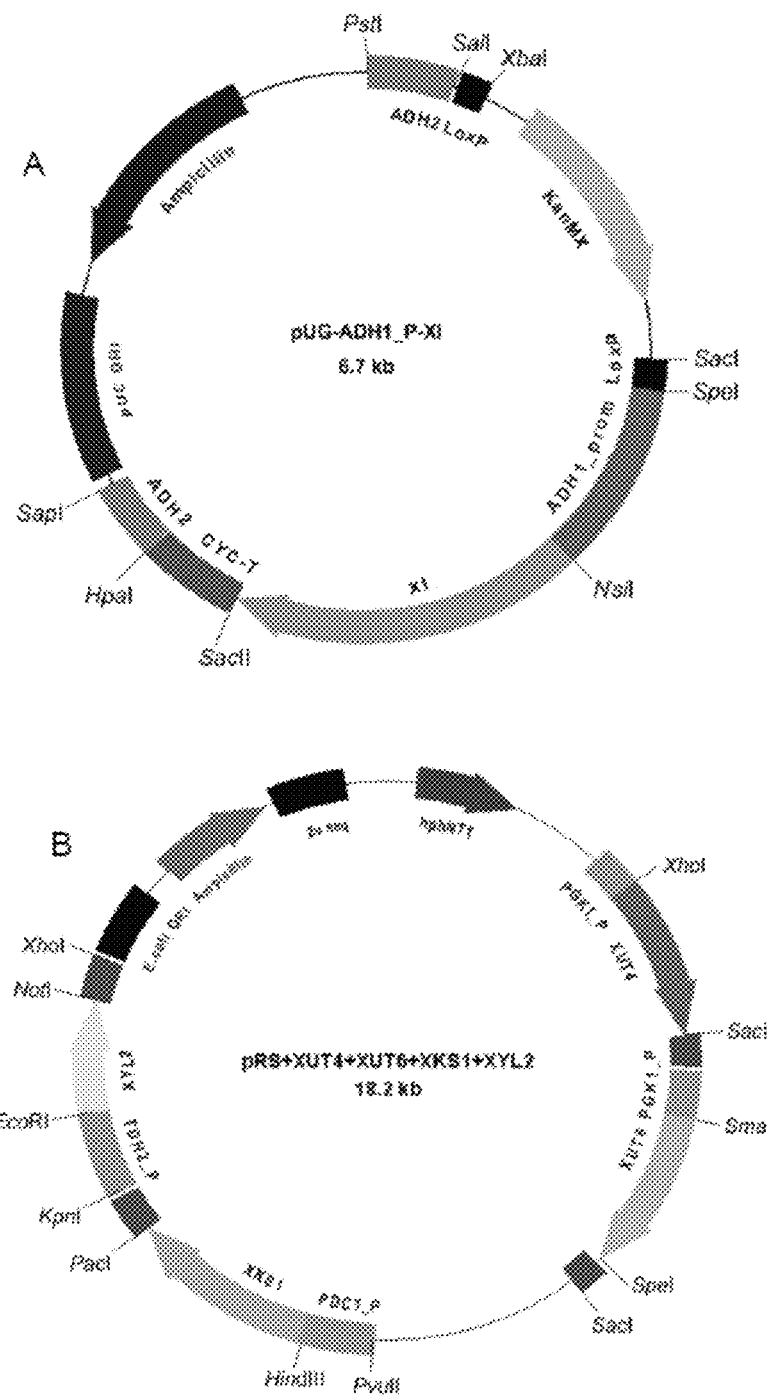
FIG. 6 depicts a vector carrying codon-optimized xylose isomerase gene YXI based on codon preference of S. cerevisiae under ADH1 promoter control for chromosomal integration at ADH2 gene site (A) and a self-replication vector (18.2 kb) containing xylose transport related genes (XUT4_ps and XUT6_ps), Xylulokinase gene (XKS1_ps) and xylitol dehydrogenase gene (XYL2_ps) for plasmid transformation (B). Relevant restriction enzyme sites and promoters are marked.

Based on robust performance evaluation of transcriptional response under aldehyde inhibitor and ethanol stress challenges, ADH1 promoter was selected for constitutive overexpression of heterologous xylose isomerase in *S. cerevisiae*. The ADH1 promoter and terminator were amplified from *S. cerevisiae* and inserted into plasmid pUG6. To realize chromosomal integration at ADH2 locus, homologous sequences of ADH2 were amplified and inserted into the new constructed plasmid. An in vitro synthesized 1317 bp YXI gene was cloned into the plasmid under ADH1 promoter control, resulting in plasmid pUG-ADH1_p-YXI (FIG. 6). A native xylose isomerase gene XylA from *C. phytofermentans* was cloned into the plasmid, resulting in plasmid pUG-ADH1_P-XylA in a similar structure as comparison studies. All necessary insertion restriction sites and primers used are provided supra.

XUT4 and XUT6 genes were amplified from *S. stipitis* NRRL Y-7124 and cloned into pRS42H under PGK1 promoter control resulting in plasmid pRS42H+XUT4 and pRS42H+XUT6, respectively. A self-replication 18.2 kb plasmid was constructed carrying two xylose transport related genes XUT4 and XUT6, xylulokinase gene XKS1, and xylitol dehydrogenase gene XYL2 from *S. stipitis* flanked by PGK1, TDH2, and PDC1 promoters and terminators respectively, resulting in plasmid pRS42H+XUT4+XUT6+XKS1+XYL2 (FIG. 6).

Yeast Transformation

Standard molecular biology techniques were performed for yeast transformation as previously described in Sambrook (supra). Plasmids of pUG-ADH1_P-XylA and pUG-ADH1_P-YXI were digested separately with PstI and SapI prior to transformation. The 4.4 kb cassette containing varied versions of xylose isomerase gene was recovered and transformed into *S. cerevisiae* strain Y-50049 using Gene Pulser Xcell Electroporation system (BioRad, Hercules, Calif.). Positive transformants were selected on YPD plate containing 200 mg $l^{-1}$ G418 followed by a PCR confirmation, resulting in strain Y-50049–XylA and Y-50049–YXI, respectively. The strain Y-50049–YXI was delivered to evolutionary adaptation on YP medium amended with 50 g $l^{-1}$ D-xylose for at least ten consecutive transfers over a period of 40 days, and the strain Y-50049–YXI_F10 was used for further plasmid transformation of pRS42H+XUT4, pRS42H+XUT6 and pRS42H+XUT4+XUT6+XKS1+XYL2, respectively. Positive transformants were selected out on a YPD plate containing 300 mg $l^{-1}$ hygromycin B and confirmed by PCR, resulting in strain Y-50049–YXI–XUT4, Y-50049–YXI–XUT6, and NRRL Y-50463.

EXAMPLE 2

Growth of Y-50463 on Xylose and Mixed Sugars in the Presence of Inhibitors

Cell growth of strain NRRL Y-50463 was evaluated on medium using xylose as sole carbon source at 20 g $l^{-1}$ or 50 g $l^{-1}$ D-xylose. Precultures were grown on a YPD medium in a 50-ml shake flask with 250 rpm agitation at 30° C. for 16 h. Cells were collected and resuspended in YP medium with D-xylose to $OD_{600}$ reading at 1.0. Two percent of resuspended cells was inoculated onto YP medium containing D-xylose in a 50-ml flask and incubated at 30° C. with agitation at 250 rpm. The parental strain Y-50049 was served as control. Cell growth performance of strain NRRL Y-50463 on mixed glucose and xylose medium was evaluated using a similar procedure with 50 g $l^{-1}$ D-glucose and 50 g $l^{-1}$ D-xylose in the presence or the absence of 10 mM each of furfural and HMF. Each assay was carried out with three replications.

Xylose metabolism in *S. cerevisiae* involves multiple steps of xylose transport, xylose-to-xylulose conversion, xylulose phosphorylation, and subsequent flux into and through the pentose phosphate pathway to central carbon metabolism pathways. Using a set of genes involving xylose utilization pathways, a genetically engineered S. cerevisiae strain designated as NRRL Y-50463 was obtained in this study carrying heterologous genes of YXI, XUT4, XUT6, XKS1 and XYL2. Strain Y-50463 was able to grow on xylose as sole carbon source (FIG. 2A). When examined on a medium with mixed sugars of 50 g $l^{-1}$ D-glucose and D-xylose, it grew continuously with a significantly higher density of cells at 96 h (FIG. 2B). In contrast, the control strain Y-50049 stopped growth after glucose was consumed after 24 h. In the presence of 10 mM furfural and HMF each, a similar cell density was reached at 120 h for Y-50463 (FIG. 2C). However, a slightly delayed in growth was observed. The growth performance of the control strain Y-50049 appeared to be similar in the presence and absence of the inhibitors but unable to utilize xylose. Introduction of a set of genes in this study extended xylose utilization capability of the tolerant yeast. On the other hand, it seemed the yeast resistance to the inhibitors was compromised slightly (FIG. 2C).

EXAMPLE 3

Gene Expression Analysis

Genetically engineered target genes were evaluated for their expression grown on xylose as sole carbon source using real time qRT-PCR. Yeast cells were harvested periodically and immediately frozen on dry ice and stored at −80° C. until use. Total RNA was isolated and RNA integrity. Primers identified in supra were designed using Primer 3, and qRT-PCR profiles and assays were performed using standard mRNA reference. Assays were performed for each condition with two biological replications and two technical replications. Electrophoresis of qRT-PCR products was also performed to examine expression of YXI, and xylose transport related gene XUT4 and XUT6 individually and in combination using mRNA harvested from two day cultures.

Previously reported bacterial XylA genes were often expressed using promoter of GAPDH, TPI1 or HXT7 in S. cerevisiae. In fact, transcription levels by these promoters are not constitutive and vary in different cell growth stages. Promoters used in plasmid construction included ADH1 promoter used for expression of YXI gene, PGK1 promoter for XUT4 and XUT6, PDC1 promoter for XKS1, and TDH2 promoter for XYL2. When transcription analysis of these heterologous genes was examined, a nearly constitutive expression over time was observed grown on xylose as sole carbon source as anticipated (FIG. 3A-C). The YXI gene under ADH1 promoter control had the highest transcription levels among the heterologous genes (FIGS. 3A and 3D). Xylose transporter genes XUT4 and XUT6 each under PGK1 promoter control was also successfully expressed (FIGS. 3E and 3F). Using ethanol- and inhibitor-tolerant promoters, constitutive and higher transcription levels of engineered heterologous genes of YXI, XKS1, XYL2, XUT4 and XUT6 in S. cerevisiae over time. Multi-copy integration of xylose isomerase gene was achieved by δ integration method for a higher level of XI expression. Apparently, more copy numbers of the desirable gene are also beneficial to improve xylose utilization.

EXAMPLE 4

Xylose Fermentation and Co-Fermentation of Mixed Sugars

Anaerobic Xylose Fermentation

Fermentation performance of strain NRRL Y-50463 using mixed sugars of glucose and xylose in the absence or the presence of furfural and HMF was evaluated using a 2-liter BioStat Fermentor at 30° C. Culture inoculum was prepared as described above and YP medium was amended with 50 g $l^{-1}$ each of D-glucose and D-xylose, and 15 mM each of furfural and HMF. The parental strain Y-50049 was served as a control. Fermentation was performed by duplicated experiments.

Anaerobic fermentation of strain NRRL Y-50463 using 50 g $l^{-1}$ D-xylose as sole carbon source was assayed at 30° C. with agitation at 250 rpm. The parental strain NRRL Y-50049 served as control. Cells were prepared using a procedure similar as described above and inoculated at ~5.0 g $l^{-1}$ dry weight cells. Duplicated experiments were carried out.

Figure 4:
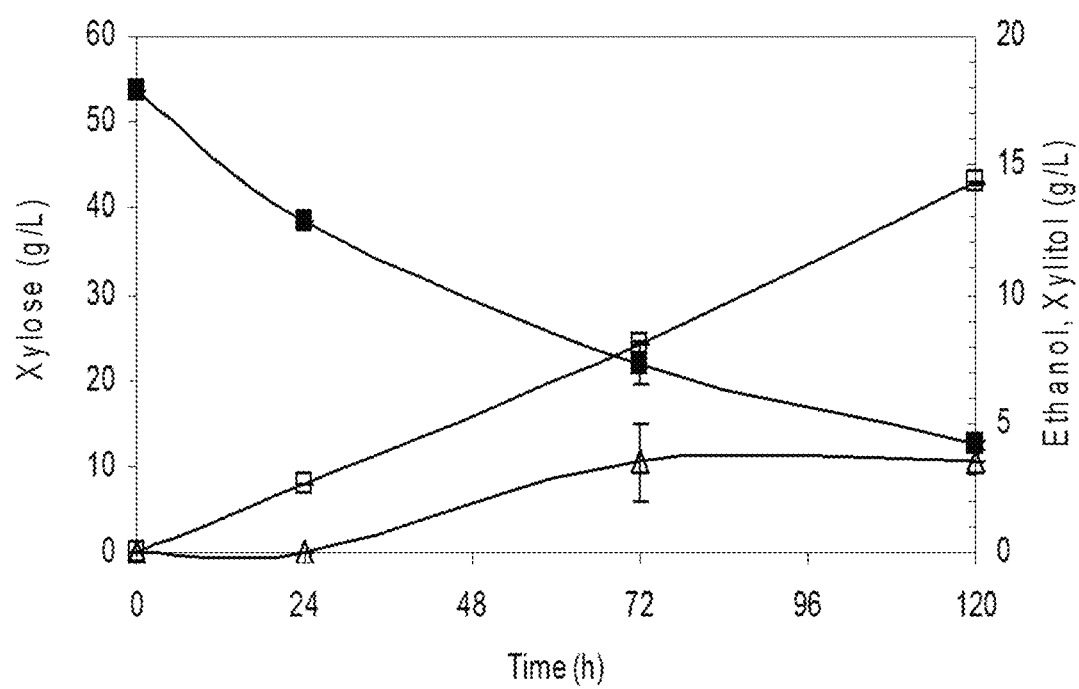
FIG. 4 depict a graph of anaerobic fermentation of xylose by *S. cerevisiae* strain NRRL Y-50463 on YP medium containing 50 g l$^{-1}$ D-xylose as sole carbon source. Filled square represents xylose, an open square for ethanol, and an open triangle for xylitol.

Using 50 g $l^{-1}$ xylose as sole carbon source, the engineered strain Y-50463 was able to produce 14.3 g $l^{-1}$ ethanol with 37.5 g $l^{-1}$ xylose consumed at 120 h in an anaerobic fermentation (FIG. 4). Its ethanol production and production rate was 0.38 g $l^{-1}$ and 0.119 g $l^{-1}$ $h^{-1}$, respectively. When mixed sugars of 50 g $l^{-1}$ D-glucose and 50 g $l^{-1}$ D-xylose were used for co-fermentation, strain Y-50463 displayed a linear consumption of xylose in 72 h. It appeared that the xylose consumption was simultaneously occurred with a rapid glucose conversion (FIG. 5A). The highest ethanol concentration of 38.6 g $l^{-1}$ was detected at 72 h with a production rate of 0.54 g $l^{-1}$ $h^{-1}$ for total consumed sugars in the absence of furfural and HMF. In the presence of inhibitors, the trend of xylose consumption was similar but the highest ethanol concentration was obtained at 96 h, a delay of less than 24 comparing with that in the absence of the inhibitors (FIG. 5B). It produced 38.6 g $l^{-1}$ ethanol with a production rate of 0.40 g $l^{-1}$ $h^{-1}$ at 96 h. As a control, the parental strain Y-50049 was unable to utilize xylose (FIG. 5C). Both Y-50463 and Y-50049 were able to convert furfural and HMF into FM and FDM under the defined fermentation conditions (FIG. 5D). In the absence of inhibitors, ethanol production kept increasing after 24 h. In the presence of the inhibitors, ethanol production rate was higher prior to 24 h but lower after 24 h comparing with that in the absence of the inhibitors. It also took more than 96 h to complete the fermentation; however, the final ethanol productions are similar. The presence of the inhibitors apparently affected the patterns of the ethanol conversion pathways.

Similarly with previous observations, xylitol was also observed as a by-product produced by this genetically engineered S. cerevisiae strain utilizing xylose. Xylitol is mainly produced from xylose by xylose reductase (XR) enzymes such as XYL1. Since heterologous XR was introduced into this yeast, the xylitol production observed is likely to be catalysed by nonspecific aldose reductase such as GRE3.

Deletion of GRE3 in previous report reduced xylitol production. However, since GRE3 involves yeast tolerance and detoxification of pretreatment inhibitors, we intend to keep it intact.

EXAMPLE 5

Cloning of Xylose-Transporter Genes XUT4, XUT5, XUT6, XUT7, RGT2, SUT4 and Vector Construction A portion of promoter and terminator for PGK1 was amplified from *S. cerevisiae* NRRL Y-50049 genomic DNA using primers PGK_PL/PGK_PR and PGK_TL/PGK_TR, as detailed in the Description of Sequences above. Amplified PGK1 fragments were cloned into vector pRS42H resulting in pRS42H -PGK1 promoter-terminator. Six putative xylose transporter genes XUT4, XUT5, XUT6, XUT7, RGT2, and SUT4 were amplified using various primers from the genomic DNA of *S. stipitis*. Each xylose transporter gene was cloned into the *S. cerevisiae* expression vector pRS42H-PGK1 promoter-terminator with proper restriction endonuclease sites designed. All DNA oligos were synthesized by IDT (Coralville, Iowa).

Each xylose transporter gene was confirmed by DNA sequencing using BigDye® Terminator v3.1 Cycle Sequencing Kit and sequencing run on an ABI 3730 DNA sequencer (Applied Biosystems, Carlsbad, Calif.). Sequences were analyzed using Sequencher v4.6 software (Gene Codes Corp. Ann Arbor, Mich.). Verified DNA sequences were deposited at NCBI GenBank under Accession numbers JF343554, JF343555, JF343556, JF343557, JF343558, and JF343559.

Six xylose transporter genes XUT4, XUT5, XUT6, XUT7, RGT2 and SUT4 were cloned and transformed into *S. cerevisiae* Y-50049–YXI, resulting in Y-50049–YXI–XUT4 (Y-50747), Y-50049–YXI–XUT5 (Y-50746), Y-50049–YXI–XUT6 (Y-50749), Y-50049–YXI–XUT7 (Y-50466), Y-50049–YXI–RGT2 (Y-50465) and Y-50049–YXI–SUT4 (Y-50748), respectively. As a control measurement, two genotypes of Y-50049–XUT4 and Y-50049–XUT6 without a functional YXI gene were also generated.

EXAMPLE 6

Xylose Utilization for Strains Y-50746, Y-50747, Y-50748, Y-50749, Y-50465, and Y-50466

The relative performance of yeast strains Y-50746, Y-50747, Y-50748, Y-50749, Y-50465, and Y-50466 containing a xylose isomerase gene and a xylose xylose transporter gene was further assessed in cell populations that were first grown aerobically on xylose and then transferred into fresh culture medium at high cell density. Under these conditions a high metabolic carbon demand creates the potential for transport to be a limiting factor and amplifies volumetric xylose consumption from the medium. Aerobic xylose uptake rate was assessed for the host strain Y-50049–YXI and each of its six xylose transporter-expressing derivatives. Duplicate precultures consisting of 250 ml of YP+50 g/L xylose each in aluminum foil-closed 1 L flasks were grown under aerobic conditions for 72 h at 30° C. and 200 rpm. The 72-h precultures were centrifuged (7000 rpm, 5 minutes) to pellet cells which were then resuspended in YP medium (without sugar) to an optical density of ~16.7 (at 600 nm). The cell suspensions were then distributed 9 ml per flask to each of 10 flasks per each strain (five xylose concentrations in duplicate). Reactions were brought to 10 ml and initiated by adding the appropriate 1-mL mix of YP (without sugar) and YP+500 g/L xylose, giving a reaction cell optical density of ~15 and the following targeted initial xylose concentrations: 5, 10, 15, 30, 50 mM. The cultures were incubated at 30° C., 250 rpm in 50-mL baffled flasks with stainless steel closures. Once xylose was added to cultures, the reaction timing began, and the first sample was immediately taken, diluted for optical density reading, and centrifuged (10,000 rpm, 6 min). The supernatant was transferred to vials and frozen at −20° C. until HPLC assay. Subsequent samples were collected at 2 h, 4 h, 6 h, and the specific xylose consumption rate (V) was calculated as the rate of decline in xylose concentration (X)/ per dry cell concentration (b), assuming the linear correlation of dry yeast biomass concentration with absorbance, b=(0.167 g/L). For each yeast strain, a Lineweaver-Burk plot of 1/V versus 1/X was prepared in order to assess $V_{max}$ and $K_m$. The relative statistical differences between strain performances due to the specific transporter gene expressed were determined by running a two-way analysis of variance of V as a function of the transporter gene and the initial xylose concentration.

Figure 7A:
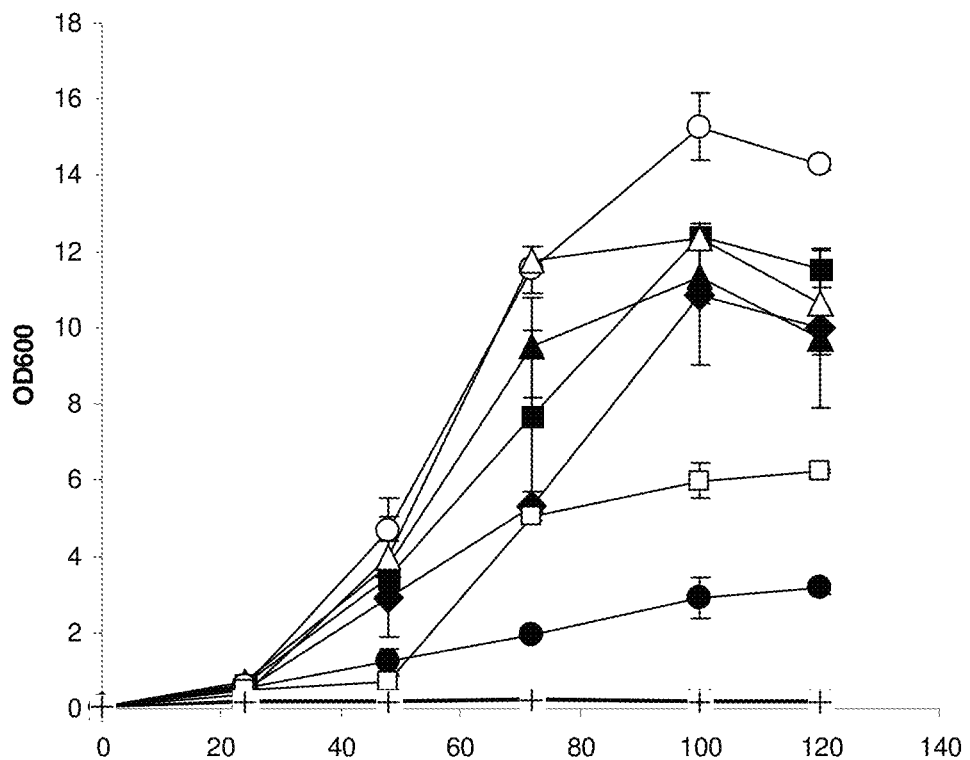
FIGS. 7A and 7B depict growth of yeast strains on xylose as sole carbon source.
Figure 7B:
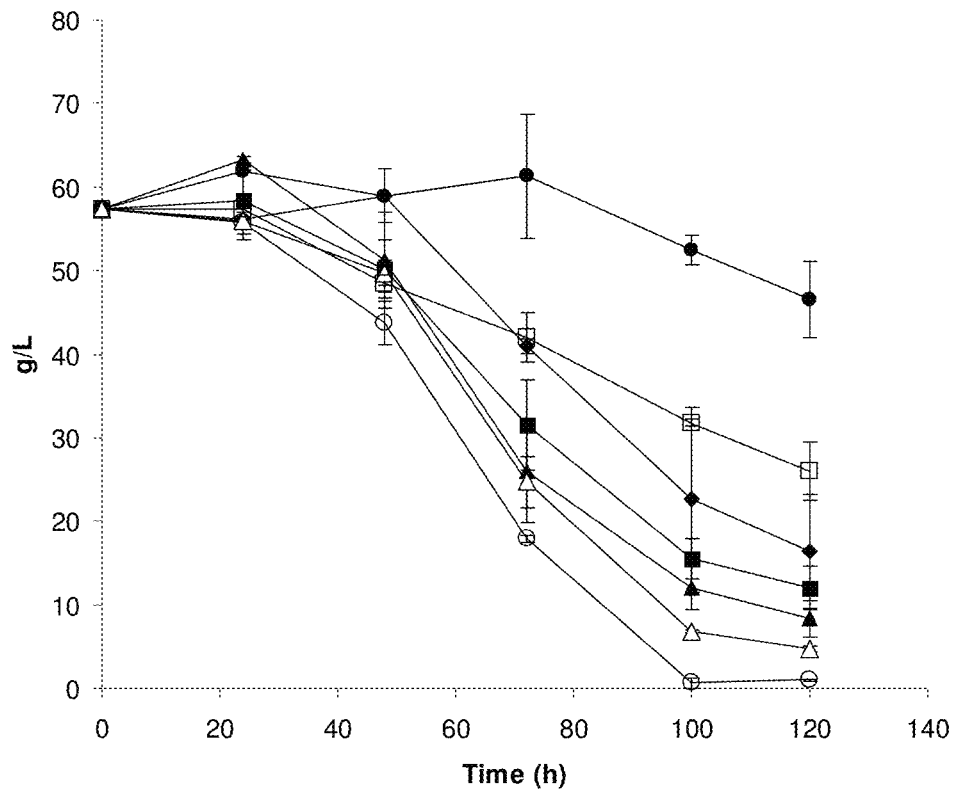

Using xylose as sole carbon source, strain Y-50049 without YXI gene and its transformant derivatives with xylose transporter genes Y-50049–XUT4 (Y-50747) and Y-50049–XUT6 (Y-50749) were unable to grow under aerobic conditions (FIG. 7A). The host strain Y-50049–YXI was able to grow on xylose at a relatively slow rate. In contrast, strains Y-50746, Y-50747, Y-50748, Y-50749, Y-50465, and Y-50466 with individual xylose transporter genes in the yeast xylose isomerase gene background showed significantly higher rates of cell growth on xylose as sole source of carbon and energy (FIG. 7A). The specific growth rate for all six strains improved up to 50% higher (Table 2). Xylose consumption over time was significantly faster and more complete for each new genotype compared with their parent Y-50049–YXI (FIG. 7B). The volumetric xylose consumption rate was significantly improved up to 7.5-fold as shown by genotype Y-50049–YXI–XUT7 (Y-50466) (Table 2).

TABLE 2

| Strain | Volumetric xylose consumption rate (g l$^{-1}$ h$^{-1}$) | Specific growth Rate (h$^{-1}$) |
| --- | --- | --- |
| Y50049-YXI | 0.071 ± 0.041 | 0.061 ± 0.010 |
| Y50049-YXI-XUT4 | 0.442 ± 0.026 | 0.091 ± 0.004 |
| Y50049-YXI-XUT5 | 0.332 ± 0.083 | 0.082 ± 0.005 |
| Y50049-YXI-XUT6 | 0.399 ± 0.036 | 0.089 ± 0.003 |
| Y50049-YXI-XUT7 | 0.535 ± 0.056 | 0.095 ± 0.003 |
| Y50049-YXI-RGT2 | 0.482 ± 0.039 | 0.095 ± 0.007 |
| Y50049-YXI-SUT4 | 0.250 ± 0.009 | 0.68 ± 0.025 |

When relative kinetic advantage was assessed among the transporter-enriched genotypes compared to the parent strain Y-50049–YXI, a significant 2.5- to 4-fold improvement of the apparent specific xylose uptake rate (V) depended on the transporter gene incorporated and the initial xylose concentration supplied ($X_o$) (Table 3). The apparent xylose uptake for all strains fit a Michaelis-Menten saturation kinetics model $V=V_{max}X/(K_m+X)$, and Lineweaver-Burk plots were applied to obtain average values for the saturation constant $K_m$ and the maximum specific uptake rate $V_{max}$ as summarized in (Table 4). All of the xylose transporter-enriched strains Y-50746, Y-50747, Y-50748, Y-50749, Y-50465, and Y-50466 tested allowed a higher affinity for xylose compared to the control, except for strain Y-50746 which had the highest $V_{max}$ but the lowest xylose affinity. Among the improved genotypes, incorporation of XUT7 in strain Y-50766 most significantly enhanced the affinity to xylose.

TABLE 3

| Strain | Overall V (h⁻¹) | $X_o = 5$ g/L | $X_o = 10$ g/L | $X_o = 15$ g/L | $X_o = 30$ g/L | $X_o = 50$ g/L |
|---|---|---|---|---|---|---|
| | | V (g/g/h) | | | | |
| Y-50049-YXI (control) | 0.082 d* | 0.041 c | 0.054 c | 0.070 d | 0.096 e | 0.150 e |
| Y-50049-YXI-RGT2 | 0.211 c | 0.112 b | 0.147 b | 0.167 c | 0.166 d | 0.461 b |
| Y-50049-YXI-SUT4 | 0.240 b | 0.144 ab | 0.172 ab | 0.236 b | 0.330 b | 0.318 c |
| Y-50049-YXI-XUT4 | 0.227 bc | 0.131 ab | 0.190 ab | 0.187 bc | 0.292 bc | 0.336 c |
| Y-50049-YXI-XUT5 | 0.336 a | 0.128 ab | 0.189 ab | 0.298 a | 0.469 a | 0.593 a |
| Y-50049-YXI-XUT6 | 0.236 bc | 0.154 ab | 0.212 a | 0.235 b | 0.267 c | 0.312 c |
| Y-50049-YXI-XUT7 | 0.224 bc | 0.185 a | 0.189 ab | 0.230 b | 0.254 c | 0.261 d |

*Within columns, means having no letters in common are significantly different using Student-Newman-Keuls pairwise comparison ($p < 0.05$).

TABLE 4

| Genotype | $V_{max}$ (g/g/h) | $K_m$ (g/L) | $R^2$ |
|---|---|---|---|
| Y-50049-YXI (control) | 0.14 | 13.26 | 0.82 |
| Y-50049-YXI-RGT2 | 0.28 | 8.10 | 0.71 |
| Y-50049-YXI-SUT4 | 0.36 | 7.83 | 0.97 |
| Y-50049-YXI-XUT4 | 0.35 | 8.74 | 0.91 |
| Y-50049-YXI-XUT5 | 0.88 | 30.58 | 0.96 |

TABLE 4-continued

| Genotype | $V_{max}$ (g/g/h) | $K_m$ (g/L) | $R^2$ |
|---|---|---|---|
| Y-50049-YXI-XUT6 | 0.33 | 5.82 | 0.97 |
| Y-50049-YXI-XUT7 | 0.26 | 2.47 | 0.80 |

EXAMPLE 7

Fermentation of Glucose-Xylose Mixtures by Strains Y-50746, Y-50747, Y-50748, Y-50749, Y-50465, and Y-50466

Fermentations of YP medium with 24.3 g $L_{-1}$ of D-glucose and 32.5 g/L D-xylose were assessed with each of the *S. cerevisiae* transformed strains in 30 ml cultures inoculated to a starting optical density of 0.05 at 600 nm ($OD_{600}$). The cultures were incubated at 30° C., 250 rpm in 50 ml flasks fitted with 22 gage needle-vented septa. This condition allows severely oxygen-limited growth of the yeast population which naturally transitions into anaerobic fermentation as cell density increases to scavenge available oxygen and carbon dioxide fills the system. Samples were taken periodically and all experiments were performed with three replications. Pre-culture growth conditions for inoculum production were as described in Example 4.

Figure 8A:
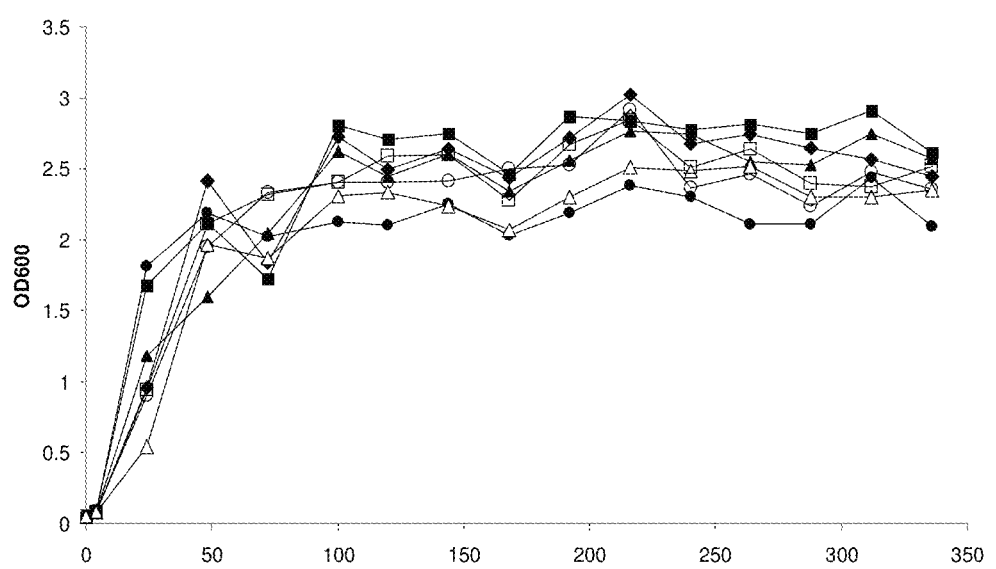
FIGS. 8A and 8B depict fermentation performance on mixed sugars of glucose and xylose of various yeast strains.
Figure 8B:
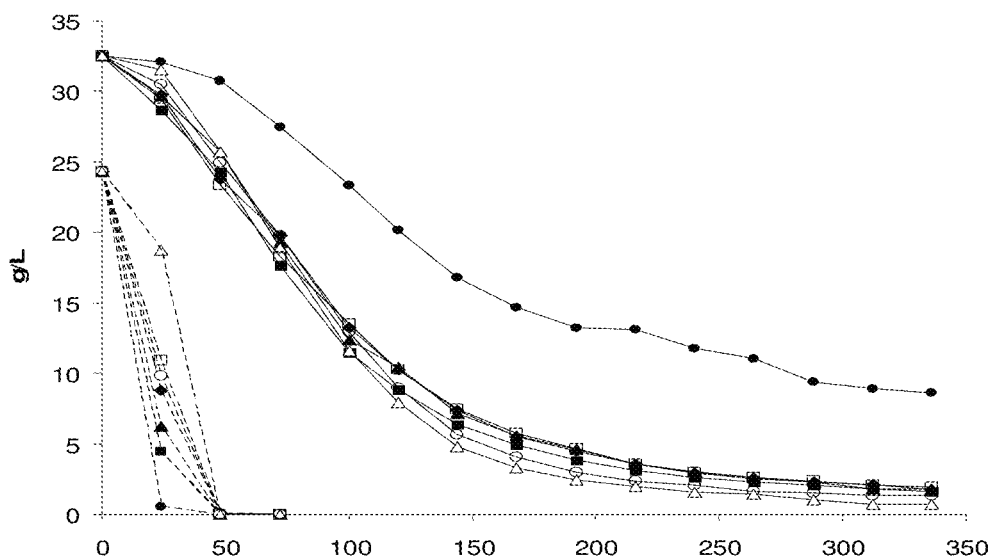

Under initial oxygen-limited conditions all genotypes tested grew similarly at relatively low cell densities of ~2 optical density units (FIG. 8A) as compared to the more abundant, but varied growth among strains observed under aerobic conditions (FIGS. 7A and 7B). As expected, glucose was quickly consumed and undetectable within 24 to 48 h (FIG. 8B). Xylose was consumed at a near linear model for all strains till 150 h but at a slower rate than glucose. However, there was no obvious glucose repression observed as commonly exhibited by recombinant *S. cerevisiae* strains.

Figure 8C:
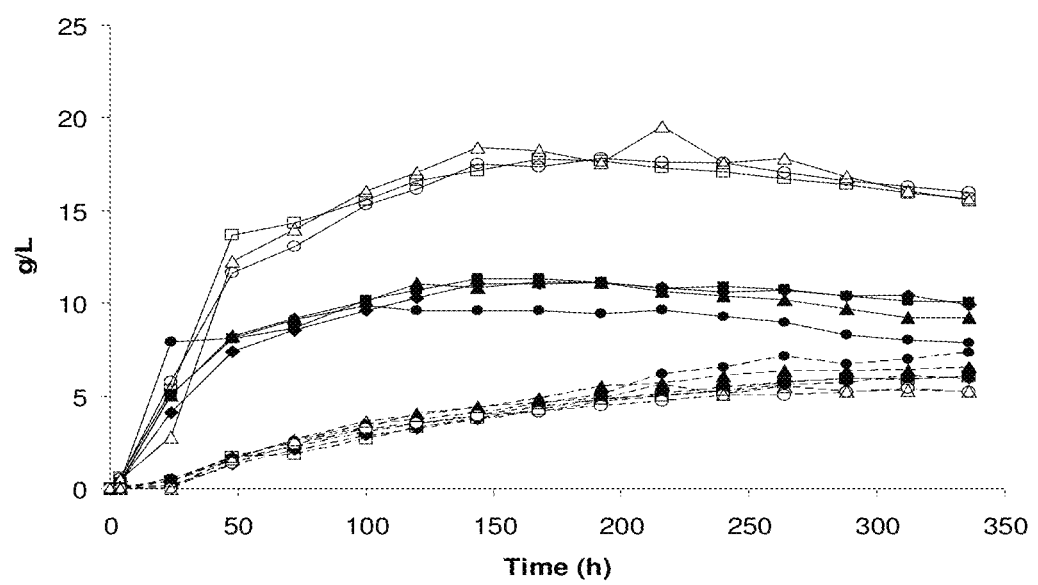
FIG. 8C depicts a graph of the same strains under the same conditions as FIG. 8A and production of ethanol as depicted by solid lines or xylitol by dotted lines for each strain.

All genotypes enriched with xylose transporter genes showed a faster xylose utilization rate than the parental control strain even when glucose was present during the first 24 h of growth (Table 5). They also showed higher levels of ethanol production and lower xylitol production than their parental strain Y-50049-YXI (FIG. 8C). Among which, genotypes containing RGT2 (Y-50465), XUT7 (Y-50466), and SUT4 (Y-50748) displayed significantly higher levels of ethanol production (FIG. 8C) than other strains. Volumetric ethanol production rate on xylose or mixtures of glucose and xylose was improved by all genotypes compared with the host strain Y-50049-YXI (Table 5).

TABLE 5

| Genotype | Glucose and Xylose Uptake (0-24 h) | | | | Xylose Uptake (48-144 h) | | Overall (0-144 h) | |
|---|---|---|---|---|---|---|---|---|
| | $O_z$ (g/L/h) | $O_x$ (g/L/h) | P (g/L/h) | Y (g/g) | P (g/L/h) | Y (g/g) | P (g/L/h) | Y (g/g) |
| Y-50049-YXI | 0.991 ± 0.004 | 0.017 ± 0.047 | 0.33 ± 0.04 | 0.33 ± 0.03 | 0.015 ± 0.011 | 0.11 ± 0.09 | 0.067 ± 0.007 | 0.24 ± 0.03 |
| Y-50049-YXI-XUT4 | 0.752 ± 0.015 | 0.118 ± 0.033 | 0.21 ± 0.03 | 0.24 ± 0.04 | 0.027 ± 0.004 | 0.14 ± 0.02 | 0.075 ± 0.003 | 0.22 ± 0.004 |
| Y-50049-YXI-XUT5 | 0.646 ± 0.024 | 0.114 ± 0.028 | 0.17 ± 0.01 | 0.22 ± 0.02 | 0.038 ± 0.004 | 0.22 ± 0.01 | 0.077 ± 0.003 | 0.22 ± 0.01 |
| Y-50049-YXI-XUT6 | 0.828 ± 0.022 | 0.159 ± 0.009 | 0.21 ± 0.02 | 0.22 ± 0.01 | 0.033 ± 0.004 | 0.18 ± 0.02 | 0.079 ± 0.004 | 0.22 ± 0.01 |
| Y-50049-YXI-XUT7 | 0.602 ± 0.021 | 0.082 ± 0.015 | 0.24 ± 0.02 | 0.35 ± 0.01 | 0.061 ± 0.003 | 0.31 ± 0.03 | 0.122 ± 0.003 | 0.34 ± 0.01 |
| Y-50049-YXI-RGT2 | 0.231 ± 0.030 | 0.040 ± 0.057 | 0.12 ± 0.01 | 0.45 ± 0.11 | 0.064 ± 0.005 | 0.29 ± 0.01 | 0.128 ± 0.005 | 0.35 ± 0.01 |
| Y-50049-YXI-SUT4 | 0.558 ± 0.032 | 0.126 ± 0.010 | 0.22 ± 0.02 | 0.32 ± 0.02 | 0.036 ± 0.007 | 0.22 ± 0.04 | 0.119 ± 0.006 | 0.35 ± 0.02 |

EXAMPLE 8

Xylose Proton Symport Assay for Strains Y-50746, Y-50747, Y-50748, Y-50749, Y-50465, and Y-50466

Cultures of the host strain Y-50049–YXI and strains Y-50746, Y-50747, Y-50748, Y-50749, Y-50465, and Y-50466 were assayed for proton symport. A modification of the method of Lucas and Van Uden was used to determine if a symport-indicative alkaline pH shift occurred upon addition of xylose to high cell density sugar-starved cultures. All S. cerevisiae strains were precultured aerobically on YP plus 50 g/L xylose as described in Example 6. As a positive control, the native pentose-fermenting yeast S. stipitis Y-7124 was transferred from YPD plates to 50 ml YP plus 50 g/L xylose preculture (25° C., 250 rpm, 24 h) to final precultures at 0.1 optical density to be cultivated 72 h similarly to the S. cerevisiae strains. The Y-7124 served as a positive control since it is known to possess both low and high-affinity xylose proton symporters. The aerobic condition used to grow cells was expected to build ATP reserves to support symport if present. The 72-h yeast cultures were centrifuged at 15° C., washed once with sugarless YP medium, then concentrated and resuspended in ~25-50 ml of the sugarless medium. The cells were allowed to starve for 2 hours at 250 rpm and 25° C. Sugar-starved cultures were resuspended to an absorbance of 140-200 in isotonic saline (9 g/L NaCl) and kept on ice until assay. Assays were conducted in a 25 ml Bellco jacketed spinner flask maintained at 350 rpm and 25° C. For recording pH readings at 0.05 sec intervals, a Broadley James FermProbe Micro, 175 mm pH probe was connected to a pH meter with analog output to an ExTech Instruments Multi-Log 720 Multimeter Datalogger. Twelve ml of isotonic saline was added to the reaction vessel, and ~4 ml of cell concentrate was added to obtain an optical density of 40. The temperature was allowed to equilibrate to 25° C. and pH was adjusted to just below 4.5 with 2-20 µl of 0.025 N HCl. After a short baseline, the symport assay was initiated by pipetting a few micro-liters of a 500 g/L xylose stock solution to achieve 7.5 g/L xylose, which was confirmed in other experiments on Y-7124 to be in excess of the $K_m$ of ~0.01-0.3 g/L xylose associated with S. stipitis symport. One-ml samples were drawn before and after the pH shift and iced immediately for subsequent absorbance determination of cell biomass and HPLC confirmation of xylose concentration.

Figure 9:
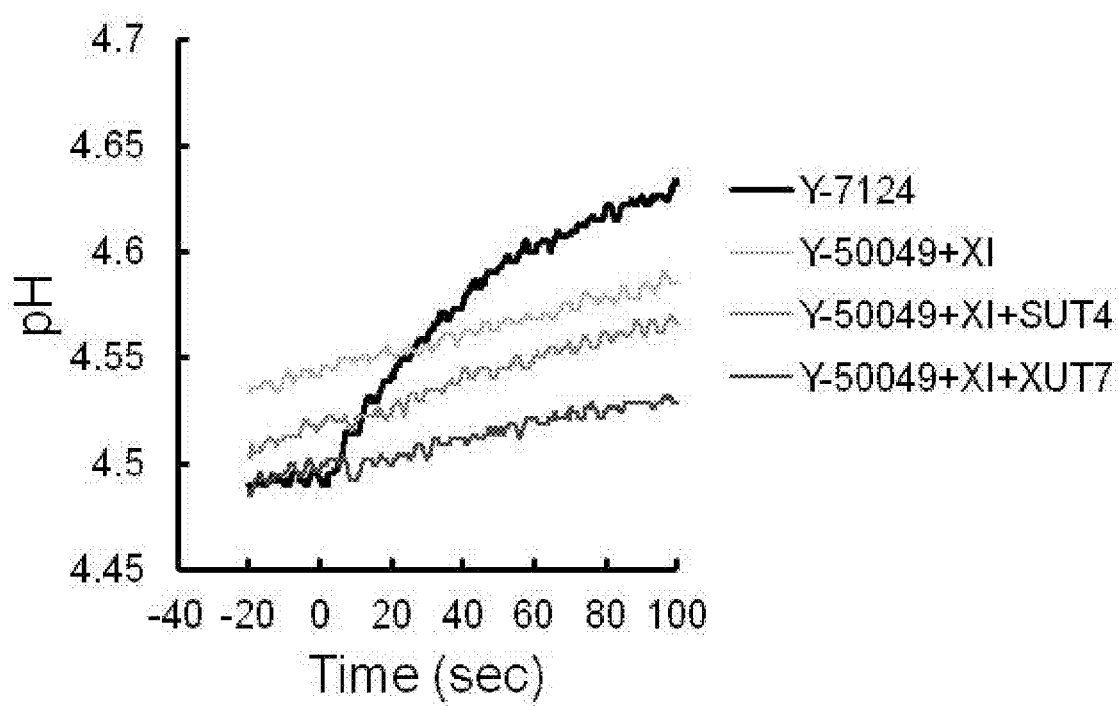
FIG. 9 depicts a graph of the pH over time for various yeast strains S. cerevisiae Y-50049–YXI, Y-50049–YXI+SUT4, and Y-50049–YXI+XUT7. A native pentose fermenting yeast, S. stipitis strain Y-7124 is also depicted.

None of the S. cerevisiae genotype tested exhibited an alkaline pH shift in response to a defined xylose spike. The typical negative pH responses observed are presented for selected genotypes in comparison with a S. stipitis positive control exhibiting the blatant alkaline shift (FIG. 9) consistent with xylose proton symport. These results indicated that none of the six xylose transporter-enriched strains were capable of xylose proton symport.

EXAMPLE 9

Expression of YXI with XUT4, XUT5, SUT4, XUT6, RGT2, and XUT7

Expression of YXI with a background of different xylose transporter genes under fermentation conditions was assayed using qRT-PCR. A culture of each xylose transporter transformed yeast strain was incubated on YPX medium at 30° C. with agitation at 250 rpm. Cell samples were collected 24 h after incubation. Total RNA extraction and qRT-PCR assays were carried out using standard mRNA quantification.

Figure 10:
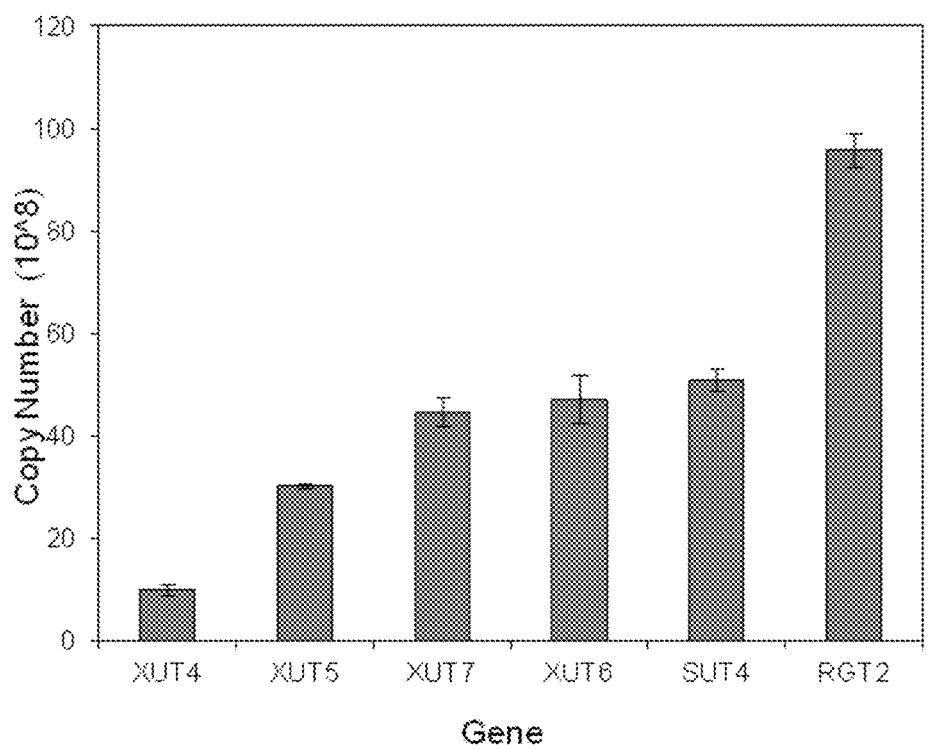
FIG. 10 is a graph depicting the expression of YXI affected by xylose transporters. Comparison of gene expression of YXI in varied genotypes enriched with varied xylose transporter genes on xylose as sole carbon source under oxygen-limited fermentation conditions 48 h after incubation. Values are means of three replications.

The genetically engineered host strain Y-50049–YXI with a synthesized YXI is able to grow on xylose as sole carbon source, and the YXI is constitutively expressed. The new genotypes enriched with individual xylose transporter genes showed further enhanced expressions of the YXI gene. The most enhanced mRNA abundance was observed for genotype Y-50049–YXI–RGT2, followed by –SUT4, –XUT6 and –XUT7 (FIG. 10). Genotypes enriched with –XUT5, –XUT4 showed modest enhancement 24 h after incubation under oxygen-limited conditions.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. A recombinant yeast strain comprising a nucleotide sequence encoding a xylose isomerase gene and a nucleotide sequence encoding xylose transporter gene, wherein the xylose isomerase gene is SEQ ID NO 63 and the xylose transporter gene is selected from the group consisting of SEQ. ID. Nos. 64, 65, 66, 67, 68, or 69.

2. A recombinant yeast strain having yeast strain Y-50049 as a parent strain comprising a nucleotide sequence encoding a xylose isomerase gene and a nucleotide sequence encoding xylose transporter gene, wherein the xylose isomerase gene is SEQ ID NO 63 and the xylose transporter gene is selected from the group consisting of SEQ. ID. Nos. 64, 65, 66, 67, 68, or 69.

3. A yeast strain deposited as NRRL Y-50465, NRRL Y-50466, NRRL Y-50746, NRRL Y-50747, NRRL Y-50748 or NRRL Y-50749.

4. A method of producing ethanol from the fermentation of xylose comprising: culturing the yeast strain of claim 1 in xylose-containing material under suitable conditions for a period of time sufficient to allow fermentation of at least a portion of the xylose to ethanol.

5. The method of claim 4, wherein the xylose-containing material further comprises glucose.

* * * * *